US00RE46275E

(19) United States
(12) Reissued Patent
Ying et al.

(10) Patent Number: US RE46,275 E
(45) **Date of Reissued Patent: *Jan. 17, 2017**

(54) NANOCRYSTALLINE APATITES AND COMPOSITES, PROSTHESES INCORPORATING THEM, AND METHOD FOR THEIR PRODUCTION

(71) Applicant: Massachusetts Institute of Technology, Cambridge, MA (US)

(72) Inventors: Jackie Y. Ying, Singapore (SG); Edward S. Ahn, Dover, MA (US); Atsushi Nakahira, Kyoto (JP)

(73) Assignee: Massachusetts Institute of Technology, Cambridge, MA (US)

( * ) Notice: This patent is subject to a terminal disclaimer.

(21) Appl. No.: 14/196,317

(22) Filed: Mar. 4, 2014

Related U.S. Patent Documents

Reissue of:
(64) Patent No.: 6,013,591
Issued: Jan. 11, 2000
Appl. No.: 09/007,930
Filed: Jan. 16, 1998

U.S. Applications:
(63) Continuation of application No. 13/536,924, filed on Jun. 28, 2012, now Pat. No. Re. 44,820, which is a
(Continued)

(51) Int. Cl.
*A61L 27/12* (2006.01)
*C03C 4/00* (2006.01)
(Continued)

(52) U.S. Cl.
CPC ..... *A61L 27/12* (2013.01); *A61F 2/30767* (2013.01); *A61L 27/32* (2013.01); *B82Y 30/00* (2013.01);
(Continued)

(58) Field of Classification Search
CPC ..... A61L 27/12; A61L 2400/12; A61K 6/06; C04B 2235/3212; C04B 35/447; C04B 35/117; C04B 35/46; C04B 35/6262; C04B 35/645; C04B 2235/3217; C04B 2235/3232; C04B 2235/3246; C04B 2235/5445; C04B 2235/549; C04B 2235/656; C04B 2235/6567; C04B 2235/785; C04B 2235/96; C03C 4/0007; B82Y 30/00; A61F 2/30767; A61F 2310/00293; Y10S 977/776
(Continued)

(56) References Cited

U.S. PATENT DOCUMENTS 4,097,935 A 7/1978 Jarcho ..... 106/35
4,149,894 A 4/1979 Ebihara et al.
(Continued)

FOREIGN PATENT DOCUMENTS

JP 4175212 6/1992
JP 4331719 11/1992

OTHER PUBLICATIONS

Ahn, E.S., et al., "Nanostructure Processing of Hydroxyapatite-based Bioceramics," *Nano Letters,* 1(3), (2001), pp. 149-153.
(Continued)

*Primary Examiner* — Elizabeth McKane
(74) *Attorney, Agent, or Firm* — Wolf, Greenfield & Sacks, P.C.

(57) ABSTRACT

Methods for synthesis of nanocrystalline apatites are presented, as well as a series of specific reaction parameters that can be adjusted to tailor, in specific ways, properties in the recovered product. Particulate apatite compositions having average crystal size of less than 150 nm are provided. Products also can have a surface area of at least 40 $m^2/g$ and can be of high density.
(Continued)

Hydroxyapatite material is investigated in particular detail. Compositions of the invention can be used as prosthetic implants and coatings for prosthetic implants.

15 Claims, 6 Drawing Sheets

Related U.S. Application Data continuation of application No. 12/749,299, filed on Mar. 29, 2010, now Pat. No. Re. 43,661, which is a continuation of application No. 10/863,863, filed on Jun. 7, 2004, now Pat. No. Re. 41,584, which is a continuation of application No. 10/044,801, filed on Jan. 11, 2002, now Pat. No. Re. 39,196, which is an application for the reissue of Pat. No. 6,013,591.

(60) Provisional application No. 60/035,535, filed on Jan. 16, 1997.

(51) Int. Cl.

| | |
|---|---|
| ***B82Y 30/00*** | (2011.01) |
| ***C04B 35/626*** | (2006.01) |
| ***C04B 35/645*** | (2006.01) |
| ***C04B 35/46*** | (2006.01) |
| ***A61F 2/30*** | (2006.01) |
| ***A61L 27/32*** | (2006.01) |
| ***C04B 35/447*** | (2006.01) |
| ***C03C 14/00*** | (2006.01) |
| ***C04B 35/488*** | (2006.01) |
| ***C01B 25/32*** | (2006.01) |

(52) U.S. Cl.

CPC ..... *C01B 25/32* (2013.01); *C03C 4/0007* (2013.01); *C03C 4/0021* (2013.01); *C03C 14/00* (2013.01); *C04B 35/447* (2013.01); *C04B 35/46* (2013.01); *C04B 35/488* (2013.01); *C04B 35/6262* (2013.01); *C04B 35/62675* (2013.01); *C04B 35/645* (2013.01); *A61F 2310/00239* (2013.01); *A61F 2310/00293* (2013.01); *A61F 2310/00796* (2013.01); *A61L 2400/12* (2013.01); *C04B 2235/3212* (2013.01); *C04B 2235/3217* (2013.01); *C04B 2235/3225* (2013.01); *C04B 2235/3232* (2013.01); *C04B 2235/3244* (2013.01); *C04B 2235/3246* (2013.01); *C04B 2235/549* (2013.01); *C04B 2235/5409* (2013.01); *C04B 2235/5445* (2013.01); *C04B 2235/5454* (2013.01); *C04B 2235/608* (2013.01); *C04B 2235/656* (2013.01); *C04B 2235/6562* (2013.01); *C04B 2235/6567* (2013.01); *C04B 2235/668* (2013.01); *C04B 2235/77* (2013.01); *C04B 2235/785* (2013.01); *C04B 2235/80* (2013.01); *C04B 2235/96* (2013.01); *C04B 2235/9653* (2013.01); *Y10S 977/776* (2013.01)

(58) Field of Classification Search

USPC ..... 501/1; 106/35; 423/311, 422, 423

See application file for complete search history.

(56) References Cited

U.S. PATENT DOCUMENTS

| | | | | |
|---|---|---|---|---|
| 4,195,366 | A | 4/1980 | Jarcho et al. | 106/35 |
| 4,207,306 | A | 6/1980 | Jarcho | 423/633 |
| 4,222,128 | A | 9/1980 | Tomonaga et al. | |
| 4,274,879 | A | 6/1981 | Irvine | |
| 4,324,772 | A | 4/1982 | Conn et al. | |
| 4,330,514 | A | 5/1982 | Nagai et al. | 423/311 |
| 4,429,691 | A | 2/1984 | Niwa et al. | |
| 4,497,075 | A | 2/1985 | Niwa et al. | 501/1 |
| 4,503,157 | A | 3/1985 | Hatahira | |
| 4,708,652 | A | 11/1987 | Fujiu et al. | |
| 4,717,556 | A | 1/1988 | Kawamura et al. | |
| 4,725,358 | A | 2/1988 | Anathapadmanabhan | |
| 4,781,904 | A | 11/1988 | Tagaya et al. | |
| 4,794,171 | A | 12/1988 | Tagaya et al. | |
| 4,849,193 | A | 7/1989 | Palmer et al. | |
| 5,030,474 | A | 7/1991 | Saita et al. | 427/2.27 |
| 5,053,212 | A | 10/1991 | Constantz et al. | |
| 5,134,009 | A | 7/1992 | Ichitsuka et al. | 428/113 |
| 5,185,177 | A | 2/1993 | Kijima et al. | |
| 5,205,928 | A | 4/1993 | Inoue et al. | |
| 5,217,699 | A | 6/1993 | Tagaya et al. | |
| 5,405,436 | A | 4/1995 | Maurer et al. | 102/35 |
| 5,427,754 | A | 6/1995 | Nagata et al. | 423/308 |
| 5,441,635 | A | 8/1995 | Ichitsuka et al. | |
| 5,470,803 | A | 11/1995 | Bonfield et al. | 501/1 |
| 5,501,706 | A | 3/1996 | Arenberg | 623/16 |
| 5,522,893 | A | 6/1996 | Chow et al. | 623/4 |
| 5,542,973 | A | 8/1996 | Chow et al. | 106/35 |
| 5,545,254 | A | 8/1996 | Chow et al. | 106/35 |
| 5,549,123 | A | 8/1996 | Okuyama et al. | |
| 5,667,796 | A | 9/1997 | Otten | 424/422 |
| 5,702,677 | A | 12/1997 | Shrimp et al. | |
| 5,833,959 | A | 11/1998 | Atsumi et al. | |
| 5,858,318 | A | 1/1999 | Luo | |
| 6,441,073 | B1 | 8/2002 | Tanaka et al. | |
| 6,689,375 | B1 | 2/2004 | Wahlig et al. | |
| 6,949,251 | B2 | 9/2005 | Dalal et al. | |
| RE39,196 | E | 7/2006 | Ying et al. | |
| RE41,584 | E * | 8/2010 | Ying et al. | 501/1 |
| RE43,661 | E | 9/2012 | Ying et al. | |
| RE44,820 | E * | 4/2014 | Ying et al. | 106/35 |

OTHER PUBLICATIONS

Akao, M., et al., "Dense Polycrystalline β-Tricalcium Phosphate for Prosthetic Applications," J. of Materials Science, 17, pp. 343-346, 1982.

deBruin, J.D., et al., "Biological Responses to Calcium Phosphate Ceramics", Bone-Bonding—Reed Healthcare Communications, Ducheyne, Kokubo & Van Blitterswijk, Eds., pp. 57-72, 1992.

Fang, et al., "Fabrication of Transparent Hydroxyapatite Ceramics by Ambient-Pressure Sintering," Materials Letters, 1995, 23, 147-151.

Hench, L.L. and J. Wilson, An Introduction to Bioceramics, Chapter 1 "Introduction" pp. 1-24, L.L. Hench and J. Wilson, Eds., 1993.

Hench, L.L., "Bioceramics: From Concept to Clinic", J. American Ceramic, Society 74 [7], pp. 1487-1510 (1991).

Hench, L.L., "Bioceramics: From Concept to Clinic", J. American Ceramic Society Bulletin, vol. 72, No. 4, pp. 93-98 (Apr. 1993).

Jarcho, M., et al., "Hydroxylapatite Synthesis and Characterization in Dense Polycrystalline Form", J. of Materials Science, 16., pp. 809-812 (1981).

Kawamoto et al., "Coating of β-Tricalcium Phosphate on Yttria-Partially Stabilized Zirconia Using Magnesium Metaphosphate as an Interlayer", *The Ceramic Society of Japan,* 99(1): 19-22 (1991).

Krajewski et al., "Spectrometric Study of the Thermal Evolution of Mechanochemically Prepared Hydroxyapatite-based Powders," *Cryst. Res. Technol.,* 31(5): 637-646 (1996).

Niihara K., et al., "New Nanocomposite Structural Ceramics", Nanophase and Nanocomposite Materials, S. Komarneni, J.C. Parker, G.J. Thomas, Eds. Mat. Res. Soc. Symp. Proc. vol. 286, pp. 405-412, (1993).

Siegel, R.W., "Recent Progress in Nanophase Materials", Processing and Properties of Nanocrystalline Materials, C. Survanaravana, J. Singh and E.H. Froes, Eds. The Minerals, Metals and Materials Society, 1996.

(56) References Cited

OTHER PUBLICATIONS

Toriyama et al., "Bending Strength of Hydroxyapatite Ceramics Containing α-Tricalcium Phosphate" *The Ceramic Society of Japan,* 95(4): 92-94 (1987).
Toriyama et al., "Effect of MgO Addition on Bending Strength of Sintered β-Tricalcium Phosphate Prepare by Mechanochemical Synthesis" *The Ceramic Society of Japan,* 95(8): 68-70 (1987).
Toriyama et al., "Effect of Mixed Addition of $Al_2O_3$ and $SiO_2$ on Mechanical Strength of Sintered β-Tricalcium Phosphate" *The Ceramic Society of Japan,* 96(8): 837-841 (1988).
Toriyama et al., "Estimation of Biocompatibility of High Strength β-Tricalcium Phosphate Ceramics by a Tissue Culture Method" *The Ceramic Society of Japan,* 98(4): 404-407 (1990).
Toriyama et al., "Sinterable Powder of Mechanochemically Synthetic β-Tricalcium Phosphate" *The Ceramic Society of Japan,* 95(7): 741-745 (1987).
Toriyama et al., "Thernal Change of Calcium Deficient Apatite Obtained by Mechanochemical Treatment" *The Ceramic Society of Japan,* 97(5): 554-558 (1989).
Toriyama et al., "β-Tricalcium Phosphate Coating on Alumina Ceramic" *The Ceramic Society of Japan,* 98(9): 1054-1057 (1990).
Toriyama et al., "Synthesis of Hydroxyapatite-Based Powders by Mechano-Chemical Method and Their Sintering," *Journal of the European Ceramic Society,* 16: 429-436 (1996).
Uematsu, et al., "Transparent Hydroxyapatite Prepared by Hot Isotactic Pressing of Filter Cake," J. American Ceramic Society, 1989, 72 (8), 1476-1478.
Webster, T.J., "Enhanced Functions of Osteoblasts on Nanophas Ceramics," *Biomaterials* 21 (2000) 1803-1810.
Webster, T.J., "Osteoblast Adhesion on Nonophase Ceramics," *Biomaterials* 20 (1999) 1221-1227.
Yokogawa et al., "Apatite Coating on Yttria Doped Partially Stablized Zirconia Plate in the Presence of Water Vapor" *The Ceramic Society of Japan,* 100(4): 602-604 (1992).
Yokogawa et al., "Tricalsium Phosphate Coating on Zirconia by Using Calcium Metaphosphate and Tetracalcium Phosphate" *The Ceramic Society of Japan,* 99(3): 211-214 (1991).
Yokogawa et al., "Preparation of Trimagnesium Phosphate by Mechanochmical Reaction" *The Ceramic Society of Japan,* 99(2): 150-152 (1991).
[No Author Listed] Definition of "acicular" from The American Geological Institute. Dictionary of Geological Terms. Published 1984. 3rd Edition: p. 4.
Gránásy et al., Growth and form spherulites. American Physical Society. Physical Review E. Jul. 19, 2005. 72 (011605):1-15. DOI: 10.1103/PhysRevE.72.011605.
M. Jarcho, et al., "Hydroxylapatite Synthesis and Characterization in Dense Polycrystalline Form", J. of Materials Science, 11, pp. 2027-2035 (1976), no month.
M. Akao et al., "Mechanical Properties of Sintered Hydroxyapatite for Prosthetic Applications", J. of Materials Science, 16, pp. 809-812 (1981), no month.

* cited by examiner

NANOCRYSTALLINE APATITES AND COMPOSITES, PROSTHESES INCORPORATING THEM, AND METHOD FOR THEIR PRODUCTION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATION

[This non-provisional application claims the benefit under Title 35, U.S.C. §119(e) of co-pending U.S. provisional application serial No. 60/035,535, filed Jan. 16, 1997, entitled "Nanocrystalline Apatites and Composites, Prostheses Incorporating Them, and Method for Their Production" by Jackie Y. Ying et al., incorporated herein by reference.] *This application is a continuation re-issue of application Ser. No. 13/536,924, filed Jun. 28, 2012 now U.S. Pat. No. Re. 44,820, which is a continuation re-issue of U.S. Pat. No. Re. 43,661, issued Sep. 18, 2012, filed as application Ser. No. 12/749,299, filed Mar. 29, 2010, which is a continuation re-issue of U.S. Pat. No. Re. 41,584, issued Aug. 24, 2010, filed as application Ser. No. 10/863,863, filed Jun. 7, 2004, which is a continuation re-issue of U.S. Pat. No. Re. 39,196, issued Jul. 18, 2006, filed as application Ser. No. 10/044,801 on Jan. 11, 2002, which is a reissue of U.S. Pat. No. 6,013,591, issued Jan. 11, 2000, entitled NANOCRYSTALLINE APATITES AND COMPOSITES, PROSTHESES INCORPORATING THEM, AND METHOD FOR THEIR PRODUCTION, filed as application Ser. No. 09/007,930 on Jan. 16, 1998, which claims priority to U.S. provisional application Ser. No. 60/035,535, filed Jan. 16, 1997, all of which are incorporated herein by reference.*

*Notice: More than one reissue application has been filed for the reissue of U.S. Pat. No. 6,013,591. The reissue applications are patent application Ser. Nos. 10/044,801 filed Jan. 11, 2002, 10/863,863 filed Jun. 7, 2004, which is a continuation re-issue of patent application Ser. No. 10/044,801; Ser. No. 12/749,299 filed Mar. 29, 2010, which is a continuation re-issue of patent application Ser. No. 10/863,863; Ser. No. 13/536,924 filed Jun. 28, 2012, which is a continuation re-issue of patent application Ser. No. 12/749,299; and the instant application which is a continuation re-issue of patent application Ser. No. 13/536,924.*

FIELD OF THE INVENTION

The present invention relates generally to bioceramics and more particularly to a class of apatite materials and composites incorporating these materials that are useful as prostheses, or coatings for prosthesis, and methods for production of these materials.

BACKGROUND OF THE INVENTION

Biomaterials are a class of functional materials designed to interact with and become incorporated into the human body for uses such as prostheses. Unlike products obtained through bioengineering, the manufacture of biomaterials rarely requires cellular processing or a biological intermediary.

There is a need for biomimetic structures friendly to body chemistry and physiology. Goals for these biomaterials are that they possess mechanical stability for hardness, compressive strength, flexural strength, and wear resistance, controlled microstructure to develop functional gradients, controlled interfacial properties to maintain structural integrity in physiological conditions, and well-understood surface chemistry tailored to provide appropriate adhesion properties, chemical resistance, long implant life, and patient comfort.

A wide variety of biomaterials exist such as biocompatible polymers and bioceramics. Biocompatible polymers include biodegradable polymers for use in providing structural support to organs and other body parts, drug delivery, and the like, and non-biodegradable polymers such as polymer prosthesis. For example, hip joint replacements typically make use of non-biodegradable polymers. The technique typically requires a traumatic in vivo polymerization reaction within the cup of a hip joint, and the use of a metal ball joint within the cup which can result in stress shielding (described below), causing bone dissolution. Uneven wear rates between the metal ball joint and the polymer sockets can cause the polymer to disintegrate within the body causing even more rapid dissolution. As a result, the interface between the metal ball joint and bone often loosens over time causing the patient great discomfort. The result is that hip joint replacement using current state-of-the-art technology may have to be performed more than once in a patient.

Bioceramics have found widespread use in periodontic and orthopedic applications as well as oral, plastic, and ear, nose, and throat surgery. Common materials for bioceramics are alumina, zirconia, calcium phosphate based ceramics, and glass-ceramics. Bioceramics can be categorized according to their in vivo interaction, typically as bioinert, bioactive, and resorbable bioceramics. Various types of bioceramics undergo fixation within the body according to different processes. Some processes are generally more favorable than others, but in many cases a bioceramic material that undergoes fixation within the body via one advantageous interaction may be associated with other disadvantages.

Bioinert bioceramics include single crystal and polycrystalline alumina and zirconia, and are characterized as such because the body encapsulates the ceramics with fibrous tissue as a natural mechanism in recognition of the inert ceramic as a foreign object, and tissue growth associated with this reaction is used to mechanically fix the ceramic article in the body. In dense alumina and zirconia, the tissue grows into surface irregularities. In porous polycrystalline alumina, zirconia, etc., tissue grows into the pores.

Resorbable bioceramics include tricalcium phosphate, calcium sulfate, and calcium phosphate salt based bioceramics. They are used to replace damaged tissue and to eventually be resorbed such that host tissue surrounding an implant made of the resorbable ceramic eventually replaces the implant.

Bioactive bioceramics include hydroxyapatite bioceramics, glass, and glass-ceramics. A "bioactive" material is one that elicits a specific biological response at its surface which results in the formation of a bond with tissue. Thus, bioactive materials undergo chemical reactions in the body, but only at their surfaces. These chemical reactions lead to chemical and biological bonding to tissue at the interface between tissue and a bioactive implant, rather than mere ingrowth of tissue into pores of the implant which provide mechanical fixation. A characteristic of bioactive ceramic articles is the formation of a hydroxycarbonate apatite (HCA) layer on the surface of the article. The degree of bioactivity is measured in terms of the rate of formation of HCA, bonding, strength, and thickness of the bonding layer as well as cellular activity.

Although many ceramic compositions have been tested as implants to repair various parts of the body, few have achieved human clinical application. Problems associated with ceramic implants typically involve the lack of a stable interface with connective tissue, or a lack of matching of the mechanical behavior of the implant with the tissue to be replaced, or both (L. L. Hench, "Bioceramics: from Concept to Clinic", J. Am. Ceram. Soc., 74, 1487-1510 (1991)). In the case of bioinert bioceramic materials, only a mechanical interlock is obtained, and if the mechanical fixation between the surrounding tissue and implant is not strong enough, then loosening of the bioceramic can occur causing necrosis of the surrounding tissue along with total implant failure. For example, when alumina or zirconia implants are implanted with a tight mechanical fit within the body and movement does not occur at the interface with tissue, they are clinically successful. However, if movement occurs, the fibrous capsule surrounding the implant can grow to become several hundred microns thick and the implant can loosen, leading to clinical failure.

Problems long associated with resorbable bioceramics are the maintenance of strength, stability of the interface, and matching of the resorption rate to the regeneration rate of the host tissue. Furthermore, the constituents of resorbable biomaterials must be metabolically acceptable since large quantities of material must be digested by cells. This imposes a severe limitation on these compositions.

The success of bioceramic implants depends upon properties of strength, fatigue resistance, fracture toughness, and the like. These properties are reported to be a function of grain size and purity, but strength typically decreases as grain size increases. High temperature sintering of β-tricalcium phosphate results typically in micron scale grains (Akao, et al., "Dense Polycrystalline β-tricalcium Phosphate for Prosthetic Applications", J. Mat. Sci., 17, 343-346 (1982)). It has been reported that an increase in the average grain size of polycrystalline $\alpha$-$Al_2O_3$ to greater than 7 microns can decrease mechanical properties by about 20% (Hench J. Am. Ceram. Soc., referenced above). Additionally, as strength is increased, porosity typically decreases according to prior art liquid phase and solid state sintering techniques (Hench, et al., Ed., Introduction to Bioceramics, Chapter 1, pages 17-20 (1993)).

One problem associated with hard tissue prosthesis, for example, artificial bones or bone portions, is "stress shielding". This phenomenon results when a prosthesis of relatively high Young's modulus, such as alumina, is used as an implant against bone. The higher modulus of elasticity of the implant results in its carrying nearly all the load. This prevents the bone from being loaded, a requirement for bone to remain healthy and strong. That is, stress shielding weakens bone in the region where a load applied to the bone is lowest or in compression. Bone that is unloaded or loaded in compression undergoes a biological change that leads to bone resorption. The elastic modulus of cortical bone ranges between 7 and 25 GPa, which is 10 to 50 times lower than that of alumina. The modulus of cancellous bone is significantly lower than that of cortical bone. The modulus of elasticity of a variety of materials used for load bearing implants is compared with the modulus values of cortical bone and cancerous bone in Hench, et al., Ed. Introduction to Bioceramics, referenced above.

Hydroxyapatite, $Ca_{10}(PO_4)_6(OH)_2$, is an attractive and widely utilized bioceramic material for orthopedic and dental implants because it closely resembles native tooth and bone crystal structure. Though hydroxyapatite is the most common bioceramic, applications for its use have been limited by its processability and architectural design conceptualization. Conventional processing lacks compositional purity and homogeneity. Because hydroxyapatite is difficult to sinter, dense hydroxyapatite structures for dental implants and low wear orthopedic applications typically have been obtained by high-temperature and/or high-pressure sintering with glassy sintering aids which frequently induce decomposition to undesirable phases with poor mechanical stability and poor chemical resistance to physiological conditions. Thus, conventionally-formed hydroxyapatite necessitates expensive processing and compromises structural integrity due to the presence of secondary phases. Existing methods require high forming and machining costs to obtain products with complex shapes. Furthermore, typical conventional hydroxyapatite decomposes above 1250° C. This results in a material with poor mechanical stability and poor chemical resistance.

Jarcho, et al., in "Hydroxyapatite Synthesis and Characterization in Dense Polycrystalline Form", J. Mater. Sci., 11, 2027-2035 (1976)), describe a process for forming dense polycrystalline hydroxyapatite that is "substantially stronger than other hydroxyapatite materials", and that elicits "an excellent biological response when implanted in bone" (p. 2027). A precipitation method was used and material of average grain size of from about 150-700 nm recovered. However, Jarcho, et al. report low volume fraction of pores, and report considerable grain growth during sintering even at firing temperatures of 1000° C. Jarcho, et al. achieved 99% density in some cases, but using a technique that can be impractical for forming desired shapes. M. Akao, et al., in "Mechanical Properties of Sintered Hydroxyapatite for Prosthetic Applications", J. Mater. Sci., 16, 809-812 (1981), report the compressive flexural torsional and dynamic torsional strengths of polycrystalline hydroxyapatite sintered at 1300° C. for three hours and, compare the mechanical properties of the product with those of cortical bone, dentine, and enamel. The compressive strength of the sintered hydroxy apatite was approximately 3-6 times as strong as that of cortical bone.

There is much room for improvement in the use of hydroxyapatite as implants. As reported by Hench et al., "Bioceramics: from concept to clinic", American Ceramic Society Bulletin 72, 4, 93-98 (1993), "Because (hydroxyapatite) implants have low reliability under tensile load, such calcium phosphate bioceramics can only be used as powders, or as small, unloaded implants such as in the middle ear, dental implants with reinforcing metal posts, coatings on metal implants, low-loaded porous implants where bone growth acts as a reinforcing phase, and as the bioactive phase in a composite." (p. 97). Hench, J. Am. Ceram Soc. (1991; referenced above) reports that hydroxyapatite has been used as a coating on porous metal surfaces for fixation of orthopedic prostheses, in particular, that hydroxyapatite powder in the pores of porous, coated-metal implants would significantly affect the rate and vitality of bone ingrowth into the pores. It is reported that many investigators have explored this technique, with plasma spray coating of implants generally being preferred. Hench reports, however, that long term animal studies and clinical trials of load-bearing dental and orthopedic prostheses suggest that the hydroxyapatite coatings may degrade or come off (p. 1504). Thus, the creation of new forms of hydroxyapatite having improved mechanical properties would have significant use, but the results of prior art attempts have been disappointing.

Recently, attention has been focused on nanocrystalline or nanocomposite materials for mechanical, optical and catalytic applications. By designing materials from the cluster level, crystallite building blocks of less than 10 nm are possible, through which unique size-dependent properties such as quantum confinement effect and superparamagnetism can be obtained. Various nanocrystalline ceramics for structural applications have been especially rigorously investigated in the 1990's. R. Siegel discusses nanophase metals and ceramics in "Recent Progress in Nanophase Materials", in Processing and Properties of Nanocrystalline Materials, C. Suryanarayana, et al., Ed., The Minerals, Metals & Materials Society (1996), noting that while many methods exist for the synthesis of nanostructured materials, including chemical or physical vapor deposition, gas condensation, chemical precipitation, aerosol reactions, and biological templating, synthesis and processing methods for creating tailored nanostructures are sorely needed, especially techniques that allow careful control of surface and interface chemistry and that can lead to adherent surface coatings or well-consolidated bulk materials. It is noted that in the case of normally soft metals, decreasing grain sizes of the metal below a critical length scale (less than about 50 nm) for the sources of dislocations in the metal increases the metal's strength. It is noted that clusters of metals, intermetallic compounds, and ceramics have been consolidated to form ultrafine-grained polycrystals that have mechanical properties remarkably different and improved relative to their conventional coarse-grained counterpart. Nanophase copper and palladium, assembled from clusters with diameters in the range of 5-7 nm, are noted for having hardness and yield strength values up to 500% greater than in conventionally-produced metal. It is also noted that ceramics and conventionally brittle intermetallics can be rendered ductile by being synthesized from clusters with sizes below about 15 nm, the ductility resulting from the increased ease with which the ultrafine grains can slide by one another in "grain-boundary sliding." However, synthesis of nanocrystalline or nanocomposite materials is difficult. Significant effort has been put into such synthesis and it is likely that in many or most attempts particle sizes on the nanometer scale are not recovered due to agglomeration. A delicate balance of synthetic parameters typically must be elucidated in connection with a particular set of materials.

In an article entitled, "New Nanocomposite Structural Ceramics", by Niihara, et al., the synthesis and characterization of micro- and nanocomposite structural ceramics is reported. A variety of ceramics including $Al_2O_3$/SiC, $Al_2O_3$/$Si_3N_4$, and the like were investigated. Nanocomposites including intra- and intergranular nanocomposites and nano/nanocomposites demonstrated improvement of mechanical properties and/or machinability and superplasticity.

While hydroxyapatite is used widely, and a hydroxyapatite formulation having mechanical and morphological properties advantageous for prostheses would be very useful, attempts to date have failed to produce reliable structural hydroxyapatite implants. Accordingly, it is an object of the invention to provide relatively simple techniques for synthesizing nanocrystalline apatite materials having structural and morphological properties useful for structural implants. In particular, it is an object to provide synthesis techniques that produce densified, nanocrystalline material under mild conditions including relatively low sintering temperature, reducing or eliminating decomposition and minimizing cost. It is another object to obtain apatite materials having enhanced mechanical and chemical resistance by maintaining an ultrafine microstructure in sintering through suppression of grain growth.

SUMMARY OF THE INVENTION

The present invention provides a set of compositions, articles, and methods involving apatite materials of particularly small crystal size and/or particle size that can be readily formed into a variety of products.

By carefully controlling processing parameters affecting the molecular and structural development of hydroxyapatite such as precursor type, precursor concentration, addition rate of precursors, aging time, reaction and aging temperature, and pH during synthesis, as well as by controlling parameters affecting the agglomeration of ceramic particles such as washing and drying of the as-synthesized gel, a loosely agglomerated nanocrystalline hydroxyapatite powder is obtained. By minimizing particle size, packing and densification is enhanced resulting in the fabrication of densified nanocrystalline hydroxyapatite by using a simple pressureless sintering process at relatively low sintering temperatures. By reducing crystallite size, ceramics become more ductile as the volume fraction of grain boundaries increases allowing grain boundary sliding. Nanostructured hydroxyapatite also allows superplastic net-shape forming for inexpensive production. Furthermore, by achieving smaller crystallite sizes, defect size is reduced. With minimized flaw sizes, nanocrystalline hydroxyapatite is densified with minimal or no sintering additives at substantially lower temperatures and demonstrates improved strength compared to the conventional polycrystalline hydroxyapatite. Thus, nanocrystalline hydroxyapatite possesses greater reliability and better mechanical properties compared to conventional hydroxyapatite with a coarser microstructure. Additionally, hydroxyapatite can be structurally reinforced by nanocomposite processing such as incorporating nanocrystalline zirconia into hydroxyapatite. Additionally, carbonate icons be substituted for phosphate ions in hydroxyapatite to yield carbonate apatite, both Type A and Type B.

Using wet chemical processing as the basis, synthetic approaches to obtain a variety of products: hydroxyapatite, carbonate apatite, and fluoroapatite in the form of nanocrystalline dense structures as well as high surface area powders and coatings are developed by controlling the morphology, size, and reactivity of the precipitated particles. These novel materials possess high chemical purity and phase homogeneity with tailored mechanical strength and biocompatibility. A wet chemical approach is used because it is versatile, simple, and easy to control, in terms of both the preparative reactions and the characteristics of the reaction product. Furthermore, the synthesis conditions of the wet chemical approach can be tailored to physiological conditions for biomimetic processing. When synthesized at low temperatures and at ambient pressures in an aqueous solution resembling physiological fluid, a bioactive hydroxyapatite stable in the body is produced.

In order to manipulate the processing of nanocrystalline hydroxyapatite, important processing parameters were identified. Parameters affecting the molecular and structural development, and chemistry of hydroxyapatite such as reaction and aging temperature, aging time, addition rate of $Ca(NO_3)_2$ to the basic $(NH_4)_2HPO_4$ solution, $NH_4OH$ concentration during chemical precipitation, and precursor concentration were examined. Parameters affecting the agglomeration and densification of ceramic particles such as grinding method, calcination temperature, and sintering temperature were also investigated. By reducing crystallite size, ceramics are toughened as the volume fraction of grain boundaries increases allowing grain boundary sliding. Furthermore, by achieving smaller crystallite sizes, defect size are reduced. By minimizing particle size, packing and densification can be enhanced.

In one aspect, the invention provides a composition including particulate apatite having an average apatite crystal size of less than 250 nm. In another embodiment, the invention provides an apatite composition having a surface area of at least 40 $m^2/g$.

The invention provides, according to another aspect, a method that involves precipitating apatite from a solvent as an apatite precipitate, removing the solvent from the apatite precipitate, and recovering the precipitate, particulate apatite. In the method, the recovered particulate apatite has an average crystal size of less than 150 nm.

The invention also provides a method of calcining nanocrystalline apatite at a temperature of less than 1000° C. and recovering a nanostructured apatite product having a BET surface area of at least 40 $m^2/g$ and a crystal size of less than 500 nm.

In another aspect the invention provides a particulate apatite composition having an average crystal size small enough that the composition can be sintered to a theoretical density of at least 90% by pressureless sintering. In another aspect, a method is provided comprising sintering a composition comprising an apatite to a theoretical density of at least 90% by pressureless sintering.

The invention also provides a method involving precipitating crystalline apatite from solution. The crystalline apatite has an average crystallite size of less than 250 nm and a BET surface area of at least 40 $m^2/g$. The precipitation is carried out under conditions, including temperature, in which, at a temperature at least 20° C. different from the precipitating temperature and under identical conditions other than temperature, crystalline apatite is precipitated having an average crystallite size of greater than 250 nm and a BET surface area of less than 40 $m^2/g$.

The invention also provides a method involving sintering a quantity of apatite powder at a temperature of at least 900° C. while allowing apatite phase decomposition of less than 10% in the material.

The invention also provides a composition comprising nanocrystalline apatite that has a theoretical density of at least 90% and an average grain size of less than one micron.

A method of the invention, in another embodiment, involves precipitating apatite from a solvent as an apatite precipitate. Solvent is removed from the apatite precipitate, and the precipitate, particulate apatite is recovered having an average particle size of less than 1 micron.

The invention also provides a method that involves calcining nanocrystalline apatite at a temperature of less than 1000° C. and recovering a nanostructured apatite product having a BET surface area of at least 40 $m^2/g$ and an average particle size of less than 1 micron.

The invention also includes a method involving sintering apatite in the absence of any sintering additives.

The invention also provides a composition including particulate apatite having a surface area of at least 40 $m^2/g$.

A method is provided in accordance with the invention that involves precipitating a particulate apatite from solution having a crystallite size of less than 250 nm and a BET surface area of at least 40 $m^2/g$ under conditions including temperature in which, at a temperature at least 20° different from the precipitating temperature and under identical conditions other than temperature, particulate apatite is precipitated having an average crystallite size of greater than 250 nm and a BET surface area of less than 40 $m^2/g$.

Other advantages, novel features, and objects of the invention will become apparent from the following detailed description of the invention when considered in conjunction with the accompanying drawings.

DETAILED DESCRIPTION OF THE INVENTION

Figure 1:
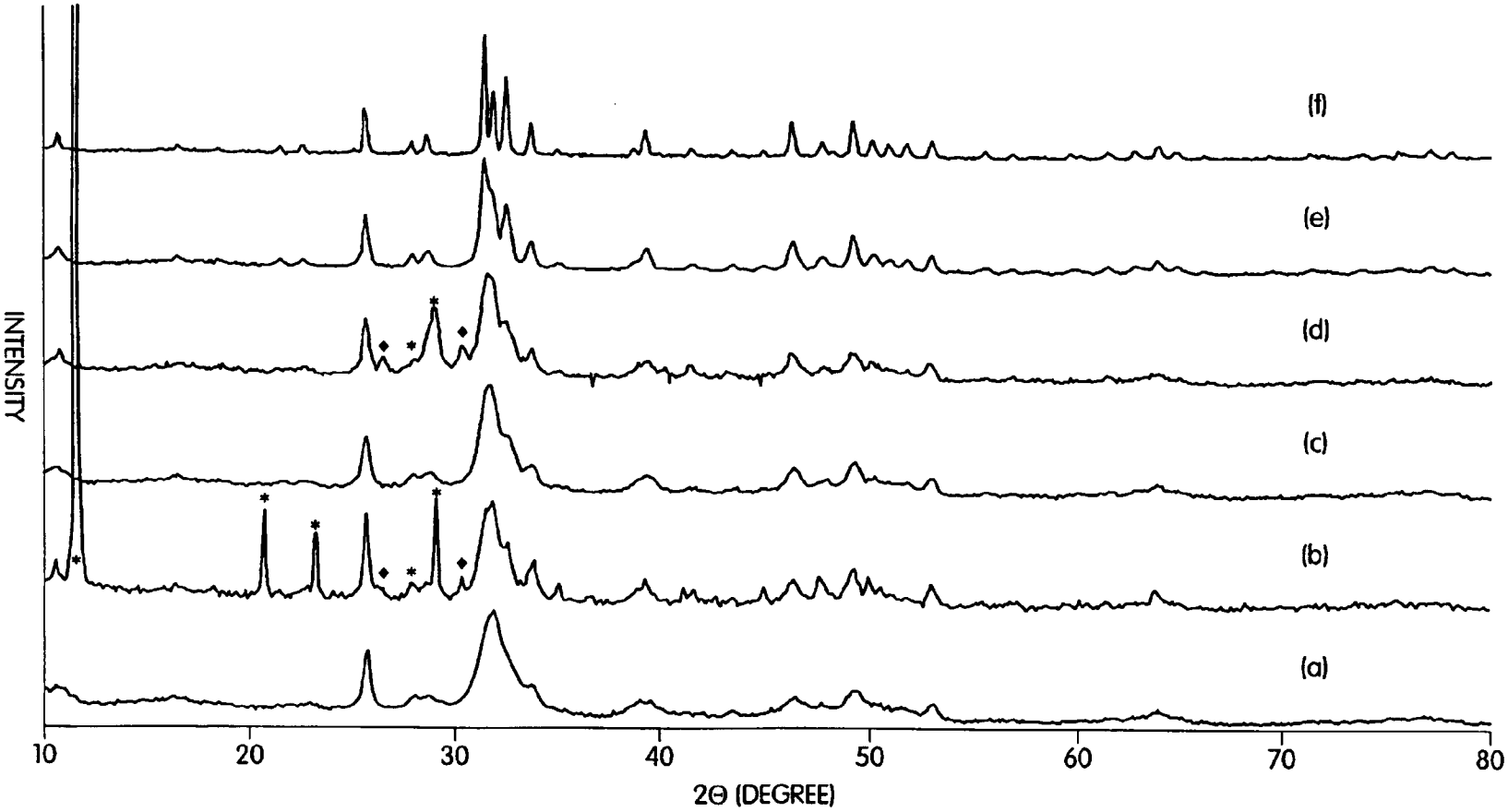
FIG. 1 is a series of x-ray diffraction (XRD) patterns of a variety of hydroxyapatite samples involving different preparation treatments.

The present invention provides methods for synthesis of nanostructured apatites, and selection criteria for process conditions and steps for carrying out related methods, that result in better microstructural control and design on the nanometer scale, phase uniformity on the molecular level, enhanced sintering behavior, greater mechanical reliability, and superplastic net shape forming. Because of exceptional microstructural control, flaw sizes are reduced which improve densification and mechanical reliability, and ultrafine domain sizes are obtained which increase ductility and superplasticity.

Nanocrystalline apatites are provided in accordance with the invention that possess greater reliability, better mechanical properties, and enhanced bioactivity compared to conventional hydroxyapatite with a micron scale microstructure. With minimized flaw sizes, nanocrystalline apatites of the invention are densified without additives at substantially lower temperatures and demonstrate unusual strength and ductility compared to the conventional polycrystalline hydroxyapatite. The nanostructured apatites not only provide superior mechanical properties but also offer the potential for superplastic net-shape forming for inexpensive rapid prototyping. Additionally, apatites can be structurally reinforced by nanocomposite processing involving incorporation of species such as zirconia into apatites.

The invention involves production of nanometer-sized compact resulting from a pressureless sintering process at relatively low sintering temperatures compared to temperatures used in known methods of producing micron-sized hydroxyapatite. A wet chemical approach is used in synthesis of preferred compositions leading to the advantages that compositional homogeneity is provided and the method is versatile and easy to control both in terms of the preparative reactions and character of the reaction product. The processing can be tailored for different applications such as densified apatites, coatings, cements, and composites by controlling the morphology, size, reactivity of the precipitated particles, and adjusting their composition.

Apatite compositions of the invention are preferably of nanocrystalline size. Crystal size typically governs bulk properties in an article, with smaller crystal sizes being advantageous for purposes of the invention. Minimization of particle size, by minimizing crystal size, makes densification of particles easier because smaller particles can re-arrange and pack more readily and have a greater driving force for densification. Accordingly, it is a goal of the invention to provide nanocrystalline apatite powder having an average particle size that approaches the average crystal size of the material. The invention involves, in preferred embodiments, a wet chemical approach in which nanocrystals are precipitated and in which the individual crystals define individual particles, followed by recovery of powder in which the crystals are agglomerated to a minimal extent, and further processing involving densification resulting in materials with useful properties.

The invention provides a method of forming ceramic material that is applicable to a wide variety of materials, including apatitic materials (apatites) such as fluoroapatites and exemplified by hydroxyapatite and carbonate apatite (Type A and Type B). Preferred bioceramics are represented by the general formula $M_{10}^{2+}(ZO_y^{3-})_6X^{2-}$, where M=Ca, Ba, Sr, Mg, Pb, Cd, etc. where M can be substituted with Na and/or K and consequently the formula can be substituted with an appropriate number of vacancies and/or anions, as known by one of ordinary skill in the art; $ZO_y$=$PO_4$, $AsO_4$, $VO_4$, etc. where $ZO_y$ can be substituted with $SiO_4$, $SO_4$, $CO_3$, $BO_3$, etc. to balance a total charge of cations, as known by one of ordinary skill in the art; and X=$F_2$, $(OH)_2$, $Cl_2$, $Br_2$, $I_2$, O, $CO_3$ etc. A preferred set of compounds are those that form hexagonally-packed crystals. Calcium-based apatites such as hydroxyapatite are particularly preferred. One set of preferred apatites include calcium phosphate apatites such as $Ca_5(PO_4, CO_3F)_3R$; $Ca_5(PO_4CO_3OH)OH$; $Ca_5(PO_4)_3Cl$; $Ca_5(PO_4)_3F$; $Ca_5(PO_4)_3OH$; $Ca_{10}(PO_4)_6 CO_3$; $Ca_{10}(PO_4)_6O$; and non-calcium phosphate apatites such as $Ba_5(PO_4)_3Cl$, $(Sr,Ce)_5(PO_4)_3OH$, $(Ce,Ca)_5(PO_4)_3(OH,F)$, $(Y,Ca)_5(PO_4)_3(OH,F)$, $Na_3Pb_2(SO_4)_3Cl$, $Na_3Ca_2(SO_4)_3OH$, $Ca_5[SiO_4,PO_4,SO_4]_3(Cl,F)$, $Pb_5(AsO_4)_3Cl$, $(Ca,Sr)_5[AsO_4,PO_4]_3OH$, $Pb_5(AsO_4)_3Cl$, $Ca_5[SiO_4,PO_4,SO_4]_3(F,OH,Cl)$, $Pb_3Ca_2(AsO_4)_3Cl$, $Ca_5[SiO_4, PO_4,SO_4]_3(OH,F,Cl)$, $Ca_5(AsO_4)_3OH$, $Pb_5(AsO_4)_3Cl$, $(Ba,Ca,Pb)_5[AsO_4,PO_4]_3Cl$, $Pb_5(PO_4)_3Cl$, $Sr_5(PO_4)_3(OH,F)$, $Ca_5(AsO_4)_3F$, $Ca_5[AsO_4,PO_4]_3Cl$, $Pb_5(VO_4)Cl$.

The invention also involves formation of nanocrystalline composites including one or more apatites with other auxiliary additives including ceramics, metals, and alloys. Ceramics preferred for use in composites include alumina, zirconia, titania, silicon carbide, silicon nitrides and other structural ceramics. Metals such as Ti, Al, Ni, W, Fe, Mo, Co, Zr, V, and other structural metals and alloys are useful. Preferably the structural additive also is nanocrystalline. The structural attitude should be selected to strengthen the composite. The auxiliary non-apatite structural component can form a major or minor component, with the overall composite having at least 10% apatite, preferably at least 20% apatite, more preferably at least 50% apatite. Composites can be formed by mixture of two or more component powders, suspension of one or more components in a solution in which one or more other components are dissolved followed by precipitation of one or more solution components, or precipitation from solution of at least two components simultaneously or nearly simultaneously. The latter technique is preferred. Zirconia and alumina are used advantageously in compositions when toughening of a composition is desired. Compositions can be formulated based on mechanical properties desired. For example, if a secondary phase is "pinned" at grain boundaries, that is, forms an intergranular phase, ultra-fine particle size may be maintained by preventing fusion of particles of the first phase, which aids densification and strengthens the material. Secondary phases that form within primary phase grains can deflect cracks, that is, prevent crack propagation within the primary phase, strengthening the material. Where a composite is formed, it is typically best if the various components are of approximately similar particle size.

A variety of simple screening tests can be used to select bioceramics that have a very high probability of forming nanocrystalline compositions in accordance with the invention. One simple test involves forming a solution of a candidate species, or reactants that can form a candidate species, precipitating the candidate species from a solution, and determining particle and crystal size of the resulting suspension using light-scattering measurements. The precipitate can be removed from solution, and XRD or microscopy such as SEM or TEM can be used to determine particle and crystal size. In this manner, for example, a large number of candidate species can be screened by simultaneously precipitating the species from a series of solutions and performing light-scattering measurements on each resulting suspension. Following this screening test, resulting precipitate can be used in accordance with the invention of the method described in greater detail below.

It has generally been relatively straightforward to make porous ceramic articles, but significantly more difficult to make dense ceramic articles. The invention provides material that can be easily densified into dense, strong material that can be used for load-bearing implants where strength is required, such as ball joints for hips, crowns for teeth, etc.

In the prior art, densification for strengthening typically has necessitated temperatures at which a particular material tends to decompose, potentially reducing biocompatibility and causing the material to degrade and reducing mechanical properties. The prior art generally teaches that, alternatively, a glassy phase (a "sintering aid," known) can be added which becomes highly viscous and flows freely during sintering but results in an interfacial glassy phase that weakens an article formed thereby.

The ability to readily densify the bioceramic material of the invention indicates that the material is of a quality that can make it very useful for uses that do not necessarily require density. That is, densification can be a screening test for a particularly useful composition, and many compositions of the invention are referred to as densifiable under certain conditions but need not necessarily be densified. The very small particle size of the invention allows formation of very dense articles.

As such, the compositions of the invention are easily formable without expensive machining because of their small crystal and particle size. Because of the small particle size of the compositions of the invention, sintering can take place at low temperatures, eliminating or minimizing decomposition. The compositions can be sintered to a high theoretical density without "sintering aids" which are known, such as glasses and glassy oxides. The compositions of the invention can be densified without external pressure at low temperature for short periods of time, for example no more than 2 hours, preferably no more than 1 hour, and more preferably no more than 30 minutes.

The invention can also be used to make relatively porous material for use in high-surface-area, flowable materials such as cement for teeth, cement for cranial surgery, and the like. In some cases, porosity can be tailored for a particular purpose such as for bone ingrowth where pores of approximately 200 microns may be desirable.

The compositions of the invention can be used as coatings. For example, thermal spray coatings, liquid-based coatings, vapor-phase coatings, coatings via wet chemical methods, and the like known in the art can benefit from the composition of the invention as the very small particle size results in higher-quality and better-adherent coatings. Porous coatings can be made by admixing an organic species with the bioceramic, forming the coating, and burning out the organic material. Similarly, self-assembled surfactants can be used to form very small pores, as described in co-pending, commonly-owned U.S. Pat. application Ser. No. 08/415,695 of Ying, et al., now abandoned, incorporated herein by reference. For larger pore articles, a polymer can be admixed with the bioceramic crystalline powder and burned out after solidification.

The bioceramic material of the invention having very small crystal sizes make it ideal for powders or coatings, and for use with bones. The crystal size of healthy bone is approximately 20-30 nm, and bioceramic material having similar crystal size will be better compatible with bone as a result. In particular, the invention provides compositions including particulate material, preferably apatite, having an average crystal size of less than 250 nm according to preferred embodiments. Preferably, the crystal size is less than 150 nm, more preferably less than 100 nm, more preferably less than 50 nm, more preferably less than 30 nm, and more preferably still less than 20 nm. In accordance with another set of preferred embodiments, the invention provides bioceramic material having a small average particle size, in particular an average particle size of less than 1 μm, preferably having an average particle size of less than 0.5 μm, more preferably still an average particle size of less than 0.25 μm. Any combination of preferred particle size and preferred crystal size can define a preferable combination of the invention, for example an average crystal size of less than 150 nm and an average particle size of less than 1 μm, etc.

The composition of the invention is particulate ceramic material, preferably apatite, that has a high surface area. In one set of embodiments the surface area is at least 40 $m^2/g$, preferably at least 60 $m^2/g$, more preferably at least 100 $m^2/g$, more preferably still at least 150 $m^2/g$. The composition of the invention is particularly robust and resistant to phase decomposition. Apatite compositions of the invention, alone or as part of a composite including an auxiliary structural additive, preferably undergoe apatite phase decomposition of less than 10% when exposed to conditions of at least 1000° C. for at least 2 hours. More preferably a composition undergoes apatite phase decomposition of less than 5%, and more preferably less than 3% under these conditions. In another set of embodiments, the composition undergoes apatite phase decomposition of less than 10% when exposed to conditions of at least 1100° C. for at least 2 hours, preferably less than 5% and more preferably less than 3% under these conditions. In another set of embodiments apatite phase decomposition of less than 10% is realized when the composition is exposed to conditions of at least 1200° C. for at least 2 hours, and apatite phase decomposition is preferably less than 5% and more preferably less than 3% under these conditions. In another set of embodiments, one exposed to conditions of at least 1300° C. for at least 2 hours such compositions undergo apatite phase decomposition of less than 10%, preferably less than 5%, and more preferable less than 3%.

The invention provides articles having a dimension of at least 0.5 cm made of any of the above-described or other compositions of the invention. The article preferably is a densified nanocrystalline apatite article where "densified" is defined as having undergone a densification step to create a self-supporting particle and, preferably, densified to a theoretical density of at least 75%. The article can be formed into the shape of a prosthesis, or can define at least part of a prosthesis such as an exterior coating on a prosthesis. When used as an exterior coating on a prosthesis, the article is at least 0.5 μm thick in at least one region, and the dimension of at least 0.5 cm is a lateral dimension relative to the article coated. The theoretical density of articles of the invention preferably is at least 90%, more preferably at least 95%, and more preferably still at least 98%. Porous articles can be provided in accordance with the invention, for example for stimulating bone ingrowth, and where porosity is desired articles having a porosity of at least 20% are preferred, more preferably the porosity is at least 30%, more preferably at least 50%, and more preferably still at least 75%.

"Densified" as used in accordance with the invention also can be defined in terms of the compressive strength of the article, with densified particles of the invention preferably having a compressive strength of at least about 150 MPa. More preferably the compressive strength of articles of the invention is at least about 500 MPa, more preferably still at least about 700 MPa.

The compositions of the invention can be provided as consolidated particulate apatite, where "consolidated" is meant to define a collection of apatite particles that forms a self-supporting structure. Apatite can be consolidated by providing particulate apatite in a press and compressing the apatite to form an article. The consolidated particulate apatite can be dense, or porous.

In all compositions, articles, and methods of the invention, preferred compositions, articles, and products of methods is hydroxyapatite, optionally in combination with an auxiliary structural additive to define a composite article.

In order to produce nanocrystalline apatites having properties tailored for a particular application, a series of processing parameters are provided in accordance with the invention that affect the molecular and structural development and chemistry of apatites, such as aging temperature, aging time, addition rate of reactants (such as addition rate of $Ca(NO_3)_2$ to basic $(NH_4)_2HPO_4$ solution in hydroxyapatite production), $NH_4OH$ concentration during chemical precipitation, and precursor concentration. Parameters affecting the agglomeration and densification of ceramic particles such as grinding method, calcination temperature, and sintering temperature also are provided. By reducing crystallite size, ceramics are toughened as the volume fraction of grain boundaries increases allowing grain boundary sliding. Furthermore, by achieving smaller crystallite sizes, defect size is reduced. By minimizing particle size, packing and densification are enhanced.

In one set of embodiments the method in the invention involves precipitating apatite from a solvent by adding a calcium salt to a phosphate source. Suitable calcium salts and phosphate sources would be recognized by those of ordinary skill in the art after reading the present disclosure. In one embodiment apatite is precipitated from a solvent containing a calcium salt in a concentration of less than 1 M, preferably less than 0.5 M, and more preferably from about 0.16 M to about 2.1 M. Preferred methods include precipitating apatite from a solvent containing a calcium salt and phosphate source in a molar ratio of about 10:6. A separate set of embodiments involves mixing a calcium source and a phosphate source in any way.

Rates of addition of calcium source to phosphate source are advantageous in many circumstances. Preferred rates are addition of calcium source to phosphate source at a rate of less than about 0.010 mols calcium source per minute, preferably less than about 0.007 mols/minute, more preferably still less than about 0.005 mols/minute. A preferred calcium source is $CaNO_3$, and a preferred phosphate source is $[NH_4]_2PO_4$.

pH has been found to be an important parameter in many circumstances, and apatite is preferably precipitated from a solvent at a pH of from about 7 to about 14, more preferably from about 11 to about 13. Apatite crystals are precipitated having a crystal size according to preferred embodiments described above, and precipitated particulate apatite having surface areas as described above, in particular preferably at least 40 $m^2/g$, 60 $m^2/g$ more preferably at least 100 $m^2/g$, and more preferably still at least 150 $m^2/g$, are recovered. It has also been found that wet grinding the resulting precipitate from the precipitation step of the invention is advantageous.

The apatite product precipitated in accordance with the invention is preferably aged at a temperature of between about −25° C. and above 100° C., more preferably between about 10° C. and about 50° C., and more preferably still approximately room temperature, i.e. about 20° C. The apatite is preferably aged for at least one minute.

The invention involves calcining nanocrystalline apatite, in a preferred set of embodiments, under a set of conditions that allow recovery of apatite product that is particularly pure and robust as described above. In preferred embodiments the recovered apatite product is of a nature such that it can be sintered at mild conditions of temperature less than 1100° C., yet results in a product having a theoretical density of at least 95% and a grain size of less than 225 nanometers. Most preferred are products which can be sintered at a temperature of less than 1000° C. resulting in a product having a theoretical density of at least 98%, and a nanostructured apatite product recovered preferably has an BET surface area of at least 40 $m^2/g$ and a crystal size of less than 250 nm.

As noted above, the invention involves a sintering technique using compositions of the invention that results in very low decomposition. Pressureless sintering preferably takes place at a temperature of no more than 1100° C. for a period of time of no more than 2 hours, more preferably no more than 1000° C. for this period of time, and more preferably still no more than 900° C. for 2 hours. Apatite phase decomposition of less than 10% occurs in this sintering step, preferably decomposition of less than 5%, preferably less than 3%. Sintering can be carried out in the absence of sintering aids. Such additives are known, and are mentioned above. Pressureless sintering is preferred and is possible because of the unique nature of the compositions of the invention. In particular, the average crystal size of particulate apatite of the invention is small enough that the composition can be sintered to a theoretical density of at least 90% by pressureless sintering, preferably at least 95%, and more preferably still at least 98% by pressureless sintering, in each case at a grain size preferably of less than 225 nanometers, at a temperature of no more than 1200° C. in one set of embodiments, more preferably no more than 1100° C., more preferably no more than 1000° C., and more preferably still the pressureless sintering to a theoretical density of 90%, 95%, or preferably 98% is carried out at a temperature of no more than 900° C. The pressureless sintering steps can be carried out to result in a densified apatite product having undergone decomposition of less than 10%, more preferably less than 5% and more preferably still less than 3%.

Another aspect of the invention involved techniques for colloidal and hot pressing of apatites. Hot pressing is a form of pressure-assisted sintering where by a pressure is applied uniaxially to a powder contained within the die during sintering under a vacuum. The pressure-assisted sintering allows for more rapid densification and a lower sintering temperature. However, because the hot pressing occurs under a vacuum, the decomposition reaction of hydroxyapatite is favored, necessitating a lower sintering temperature to prevent decomposition. Colloidal pressing (wet pressing) is a process by which a stabilized sol of hydroxyapatite is uniaxially pressed in a die. A stabilized sol of material is defined as a suspension of particles which do not undergo sedimentation appreciably over time. Frits within the die allow the solvent to escape as the die is pressurized while trapping the solid particles. Once enough solvent is removed to obtain a solid pellet, the pellet is removed and is carefully dried to prevent drying stresses from cracking the pellet. After fully drying the pellet, the pellet is CIPed and undergoes normal pressureless sintering. By avoiding a dry powder phase, colloidal pressing prevents the agglomeration associated with working with a dry powder and benefits from the lubrication effects of the solvent during pressing, which allow the particles in solution to rearrange into the densest packing. The present invention provides synthesis conditions for successful hot pressing and colloidal pressing.

As mentioned, all of the compositions and articles of the invention can include an auxiliary structural additive, and methods of the invention can involve formation of apatite material including auxiliary structural additive. The auxiliary structural additive can be a metal oxide, preferably selected from among zirconia, titania, and alumina, and/or any combination of these alone or with other known structural additives, defining a composite. The auxiliary structural additive can be added in an amount of from about 1 to about 50% by volume, preferably from about 15 to about 35% by volume. The additive can be nanocrystalline to form a "nano/nano" composite. In methods of the invention involving precipitation, apatite can be precipitated from a solvent containing, in suspension, an auxiliary structural additive, or apatite can be provided in suspension in a solvent from which is precipitated the auxiliary structural additive or, preferably, the apatite and auxiliary structural additive or additives are co-precipitated essentially simultaneously. Nanocrystalline apatite can be calcined in the presence of auxiliary structural additive and a nanostructured apatite product recovered. Similarly, sintering of the nanocrystalline apatite in the presence of the auxiliary structural additive is advantageous. Alternatively, apatite powder can be independently recovered and auxiliary structural additive independently provided (rather than precipitation from a common solvent or suspension), and admixed and sintered.

Using apatite synthesis via the wet chemistry route provided in the invention, a variety of useful applications are realized. First, nanocrystalline apatite powders are provided. Furthermore, since the nanocrystalline apatites of the invention have superior sinterability, they can be easily developed into dental and orthopedic implants requiring densified hydroxyapatite parts. Composites provided in the invention, such as zirconia-toughened apatites possess even better mechanical strength than pure apatites and have the potential as material of choice for load-bearing applications. Also, since densified apatites are provided that are thermally stable up to 1300° C., they can be used in high temperature applications. The chemical precipitation process of the invention can also be modified to provide a variety of other novel products such as coatings, cements, nanocrystalline carbonate apatites as artificial bone crystals, and nanocrystalline fluoroapatite for dental applications.

As mentioned above, the invention also involves the substitution of carbonate for hydroxide in processing resulting in Type A carbonate apatite and substitution of carbonate for phosphate in processing resulting in Type B carbonate apatite. In its broadest sense, the invention according to this aspect involves processing conditions, for carbonate apatite, according to the preferred ranges of temperature, pH, aging time, and other parameters listed above as important to the invention in connection with hydroxyapatite. In addition, for the carbonate apatite embodiment, carbonate source, method of carbonate introduction, temperature, aging time, and pH are important, especially for carbonate apatite. Products made according to these methods also are a part of the invention.

The function and advantage of these and other embodiments of the present invention will be more fully understood from the examples below. The following examples are intended to illustrate the benefits of the present invention, but do not exemplify the full scope of the invention.

EXAMPLE 1.

Synthesis and Characterization of Nanocrystalline Hydroxyapatite

A nanocrystalline hydroxyapatite powder was successfully synthesized that allowed pressureless sintering without glassy sintering aids at a remarkably low temperature of 1100° C. for 2 hours or less, resulting in a material that was >98% dense.

A series of experiments were conducted to determine the feasibility of synthesizing nanocrystalline hydroxyapatite and to determine the optimal pH, aging temperature, aging time, and heat treatment where the optimal hydroxyapatite is the sample that possesses the highest green and sintered densities. Reagant grade $Ca(NO_3)_2.4H_2O$ and $(NH_4)_2HPO_4$ were used as starting materials. Aqueous solutions of $(NH_4)_2HPO_4$ (NHP) and $Ca(NO_3)_2$ (CaN) were prepared such that the Ca:P ratio was 10:6. 0.300 M $(NH_4)_2HPO_4$ and 0.500 M $Ca(NO_3)_2$ as well as 0.100 M $(NH_4)_2HPO_4$ and 0.167 M $Ca(NO_3)_2$ were prepared. These solutions were mixed with a magnetic stirrer. The pH of the $NH_4)_2HPO_4$ aqueous solution was varied by adding concentrated $NH_4OH$. 300 ml of a 0.500 M solution of $Ca(NO_3)_2$ was added to 300 ml of 0.300 M aqueous $(NH_4)_2HPO_4$, or 900 ml of a 0.167 M solution of $Ca(NO_3)_2$ was added to 900 ml of 0.100 M aqueous $(NH_4)_2HPO_4$ solution at a rate from 2 ml/min to 48 ml/min; the number of moles of precursors was constant in both set of reactions. The combined solution was magnetically stirred for 12 or 100 hours and aged at 0° C., room temperature, or 70° C., The white precipitate was collected by centrifugation at 1500 rpm for 15 minutes. After decanting, the precipitate was redispersed in a distilled water and $NH_4OH$ solution by magnetically stirring for 20 minutes; this procedure was repeated two more times with decreasing amounts of $NH_4OH$ and a fourth and final time with ethanol. The gel was air dried at room temperature for 24 hours and then dried in a 150° C. oven for an additional 24 hours. The gel was then finely ground with an alumina mortar and pestle. Instead of air drying the gel, the gel was also wet ground. Wet grinding is a procedure by which a gel is ground in a heated mortar and pestle until the gel becomes a fine powder. The ground powders we re then heat treated in air at 550° C., 700° C. and 900° C. with a heating rate of 10° C./min, and a dwell time of 2 hours.

Pressureless Sintering

The hydroxyapatite powders heat treated at 550° C. in air were sieved and ground to a mesh size of 230. The powders were uniaxially pressed in stainless steel dies at 150 MPa. Pellets were produced using an 8 mm diameter die. From 0.15 g of sample, these compacted pellets were then cold isostatically pressed (CIPed) at 300 MPa in oil for 3 minutes. After CIPing the pellets were sintered in air atmosphere by normal pressureless sintering. Pressureless sintering was done at 1100° C. for 2 hours with a heating rate of 5° C./min. Sintering was also performed at 1000° C., 1100° C., 1200° C., 1300° C. with a heating rate of 5° C./min.

Characterization and Evaluation

Nano-hydroxyapatite powder calcined at 550° C. were characterized by photoacoustic Fourier-transform infrared spectroscopy (PA-FTIR) on a Biorad Digilab spectrometer and by X-ray powder diffraction (XRD) on a Siemens D5000 diffractometer (45kV-40mA, Cu-Kα). The XRD pattern was analyzed using a Scherrer's analysis of the (002) peak which corresponds to a d-spacing of 3.44 Å to determine the XRD crystallite size. The BET surface area and pore size distribution of nano-hydroxyapatite powder after a 550° C. heat treatment were evaluated with nitrogen adsorption analysis (Micromeritics ASAP2000). Densities of the green and sintered pellets were measured geometrically and by Archimedes method using water, respectively. The theoretical density was assumed to be 3.16 g/cc. Densified and sintered HAP pellets were characterized by XRD.

EXAMPLE 2

Determination of Optimal Conditions—Calcination, and Comparison With Commercially-Available Hydroxyapatite Powder One sample of nanocrystalline hydroxyapatite from Example 1 (Trial 2) was heat-treated in air at 550° C., 700° C., and 900° C. for 2 hours in order to investigate the effect of calcination temperature on the microstructure of hydroxyapatite; Trial 2 synthesis conditions are presented in Table 1. The XRD patterns of the as-synthesized hydroxyapatite at various calcination temperatures (FIG. 1) indicated that the sample heat treated at 550° C. had better crystallinity than the precursor gel prior to the heat treatment, although the peaks were still quite broad. The heat treatment at 700° C. gave increased crystallinity compared to the sample treated at only 550° C. and was composed of only hydroxyapatite. Even after calcination at 900° C., the sample was found to be composed of only hydroxyapatite. The XRD patterns of the as-received conventional hydroxyapatite powders (Aldrich) (FIG. 1(b)) showed the presence of $CaHPO_4.2H_2O$ (brushite) and $Ca_3(PO_4)_2$ (beta-tricalcium phosphate or β-TCP). By 700° C., this material contained substantial amount of $Ca_3(PO_4)_2$ while our nanocrystalline material gave only a pure hydroxyapatite phase.

TABLE 1

Trial 2 Synthesis Conditions

| Trial | Aging Time (hr) | Rxn/Aging Temp (° C.) | $Ca(NO_3)_2$ Addition Rate (ml/min) | Grinding Method | CaN Concentration (M) | Amount (ml) | NHP Concentration (M) | Amount (ml) | $NH_4OH$ Amount (ml) |
|---|---|---|---|---|---|---|---|---|---|
| 2 | 12 | 25 | 15 | Wet | 0.500 | 300 | 0.300 | 300 | 30 |

Figure 2:
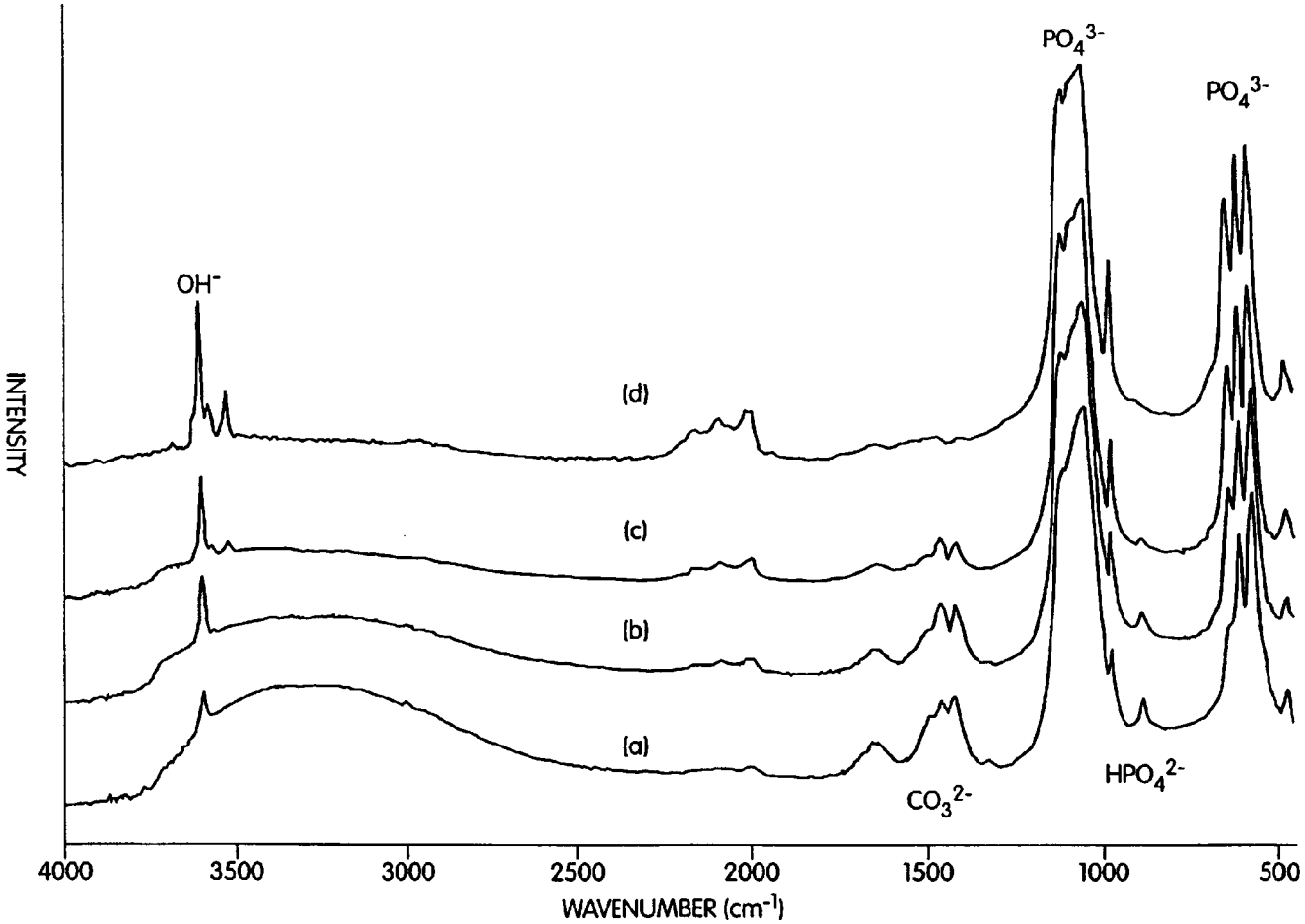
FIG. 2 is a series of Fourier Transform infrared (PA-FTIR) spectra of nanocrystalline hydroxyapatite as synthesized and after a series of treatment steps.

The effect of calcination in air on the molecular structure of the nanocrystalline hydroxyapatite powder was studied with PA-FTIR. The FTIR spectrum in FIG. 2 of the nanocrystalline hydroxyapatite powder calcined at 550° C. was similar to that of the as-synthesized hydroxyapatite precursor gel, although the peak at 875 $cm^{-1}$ associated with $HPO_4^{2-}$ was reduced. The $PO_4^{3-}$ peaks near 1030-1090 $cm^{-1}$ and at 560-600 cm–1 also became more well-resolved after calcination indicating that the hydroxyapatite structure became more defined. With increasing temperature, the broad band at 3000-3400 $cm^{-1}$ became less prominent as water was removed. The peak intensities of $CO_3^{2-}$ around 1400 $cm^{-1}$ and $H_2O$ at 1630 $cm^{-1}$ were substantially reduced.

The surface areas of nano-hydroxyapatite powder after calcination at various temperatures are summarized in Table 2. Hydroxyapatite calcined at 550° C. has a high BET surface area of 107.5 $m^2/g$, compared to 39.5 $m^2/g$ for the as-received conventional hydroxyapatite powder (Aldrich). The increase in calcination temperature decreased the surface area of nano-hydroxyapatite powder. Thus, the optimal calcination temperature for the pure nano-hydroxyapatite powder is 550° C. because phase homogeneity and high surface area are retained while volatiles are removed by this calcination temperature making the powder ideal for compaction.

TABLE 2

XRD Crystallite Size and BET Surface Area of Hydroxyapatite from TEM Observation and XRD Analysis

| Calcination Temperature (° C.) | XRD Crystallite Size (nm) | BET Surface Area ($m^2/g$) |
|---|---|---|
| as-synthesized | 40.0 | 226.6 |
| 550 | 40.0 | 107.5 |
| 700 | 75 | 42.5 |
| 900 | >100 | 9.3 |
| Aldrich (as-received) | 92 | 39.5 |

EXAMPLE 3

Determination of Optimal Conditions—Sintering, and Comparison with Commercially-Available Hydroxyapatite Powder The Trial 2 hydroxyapatite calcined at 550° C. in air was CIPed and sintered at 1000° C., 1100° C., 1200° C. and 1300° C. in air. Conventional hydroxyapatite is known to be stable up to 1360° C. (K. De Groot, C. P. A. T. Klein, J. G. C. Wolker, and J. De Blieck-Hogervorst, "Chemistry of Calcium Phosphate Bioceramics," Handbook of Bioactive Ceramics: Calcium Phosphate and Hydroxyapatite Ceramics, Vol 2, pp. 3-15, Edited by T. Yamamuro, L. L. Hench, and J. Wilson, CRC. Press, Boca Raton, 1990). The decomposition reaction is $Ca_{10}(PO_4)_6(OH)_2 \rightarrow 3Ca_3(PO_4)_2 + CaO + H_2O$ and begins at 1200° C. (K. Kamiya, T. Yoko, K. Tanaka, Y. Fujiyama, "Growth of Fibrous Hydroxyapatite in Gel System," J. Mater. Sci., 24, 827-832, 1989). It has been reported that even below 1200° C. the loss of $OH^-$ may occur (K. R. Venkatachari, D. Huang, S. P. Ostrander, W. Schulze, and G. C. Stangle, "Preparation of Nanocrystalline Yttria Stabilized Zirconia" J. Mater. Res., 10,756-761, 1995). The formation of CaO and TCP results in a weakening in mechanical properties and chemical stability. It has been reported that hydroxyapatite with lower Ca/P ratio begins to turn into β-TCP by loss of water at 800° C. (T. Kanazawa, T. Umegaki, and H. Monma, Apatites, New Inorganic Materials, Bull, Ceramic Soc. Jpn., 10, 461-468 (1975)). The temperature of decomposition is known to be dependent on the purity and Ca/P ratio of the powder. The decomposition of hydroxyapatite with a high Ca/P ratio is inhibited even at higher temperatures.

Figure 3:
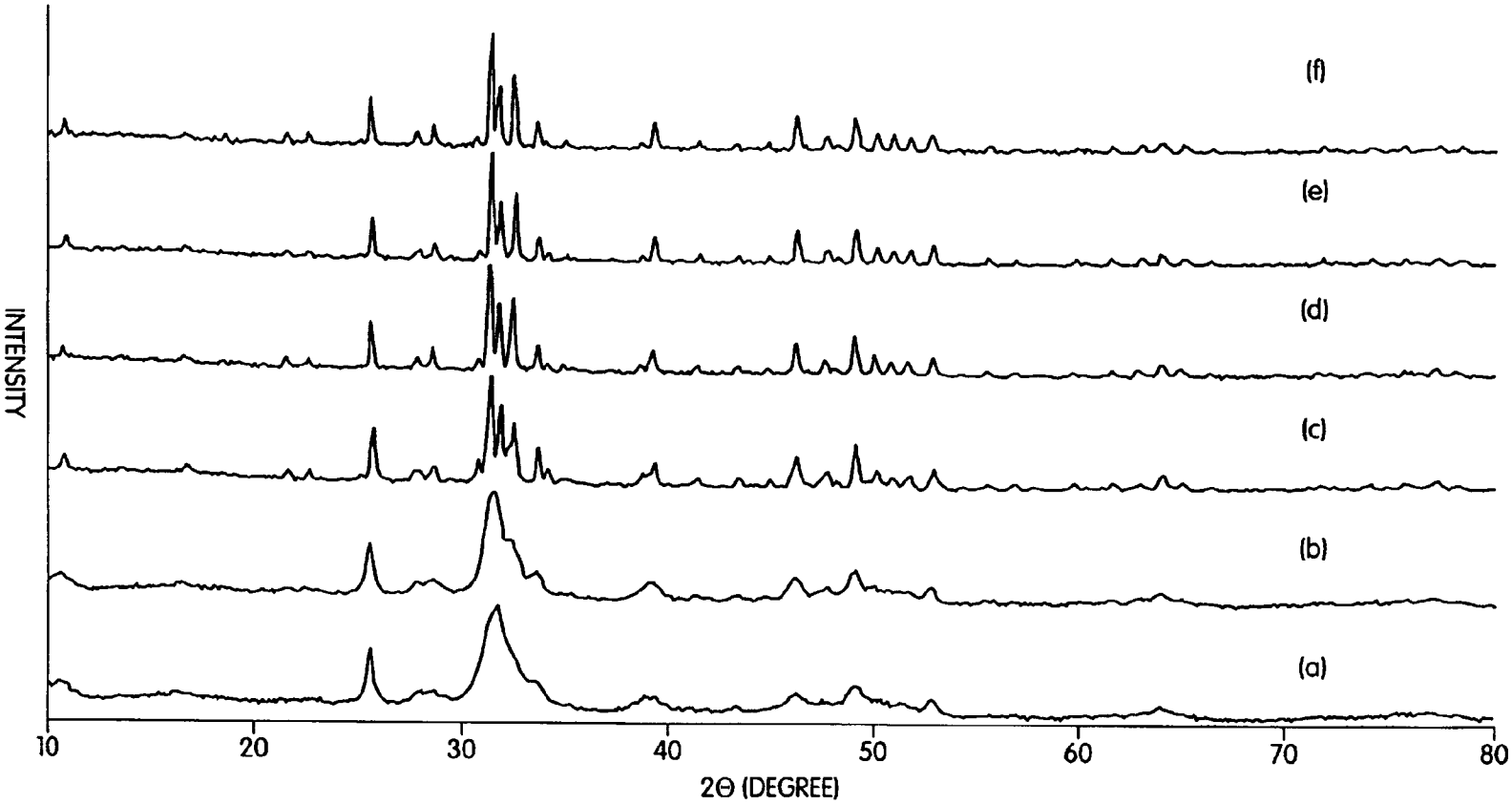
FIG. 3 is a series of XRD patterns of nanocrystalline hydroxyapatite after a series of treatment steps as in the material identified in FIG. 2.
Figure 4:
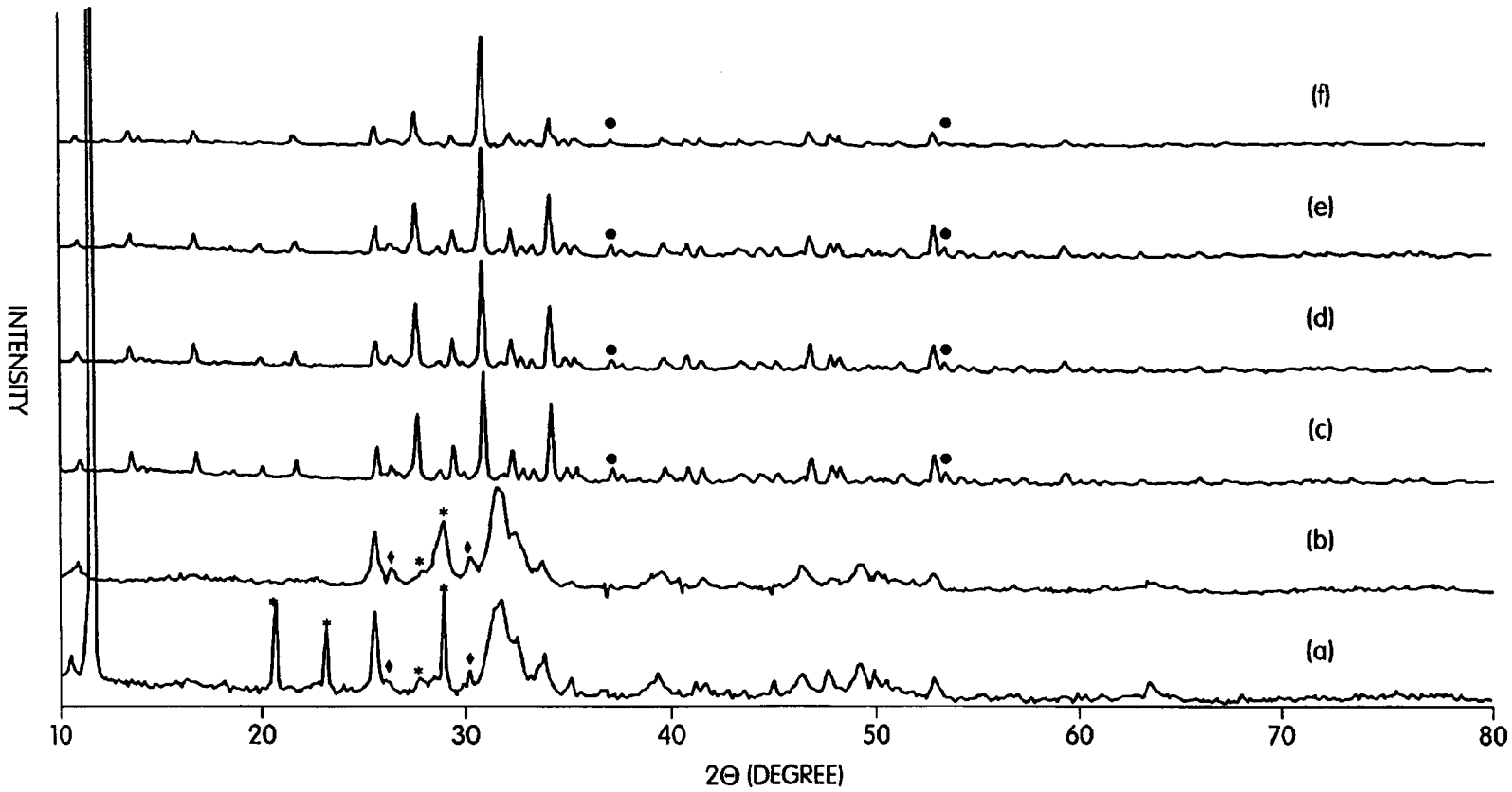
FIG. 4 is a series of XRD patterns of comparative, conventional, commercially-available hydroxyapatite as received and after a series of treatment steps.
Figure 5:
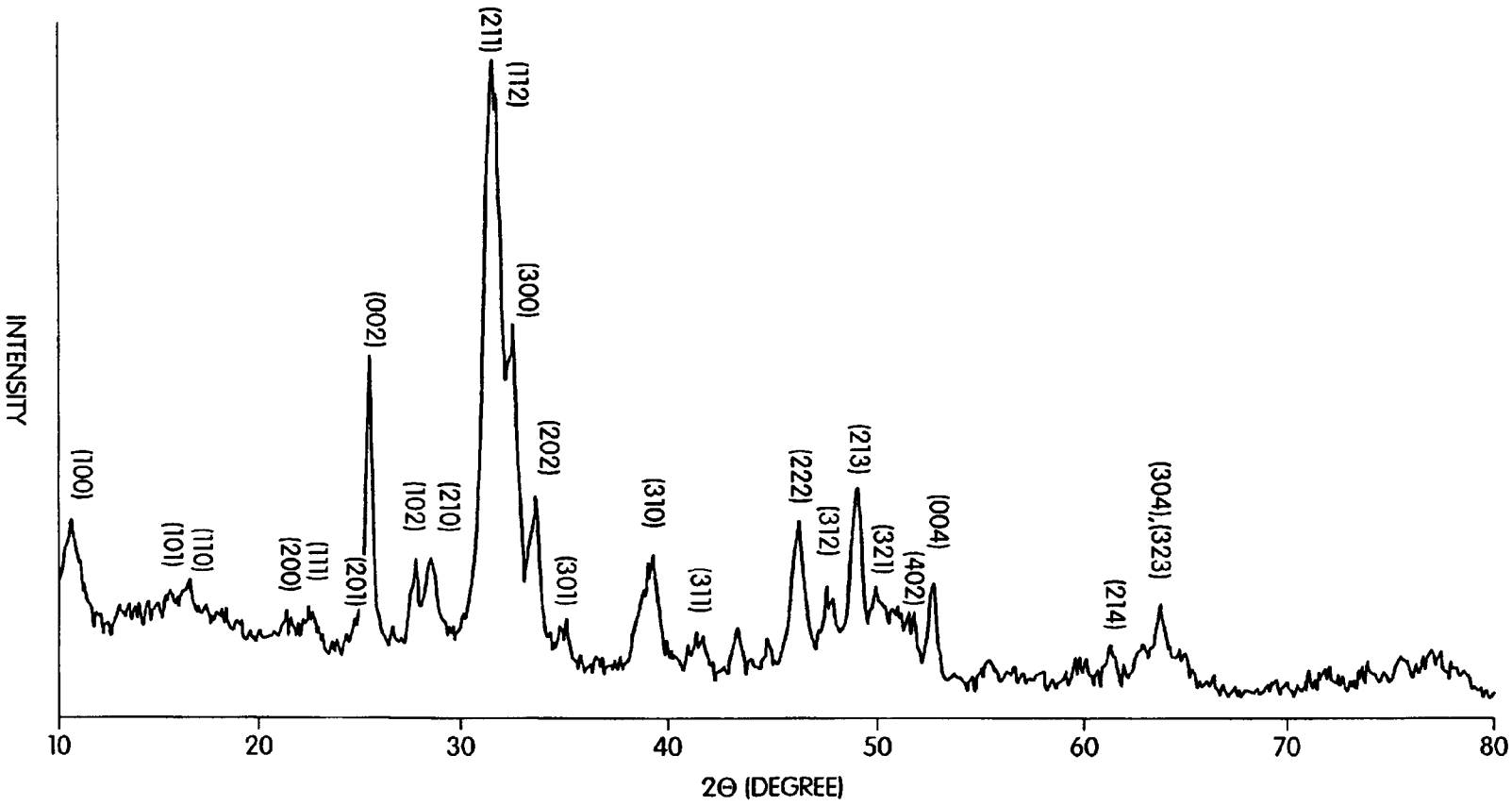
FIG. 5 is an XRD pattern of nanocrystalline hydroxyapatite after calcination.
Figure 6:
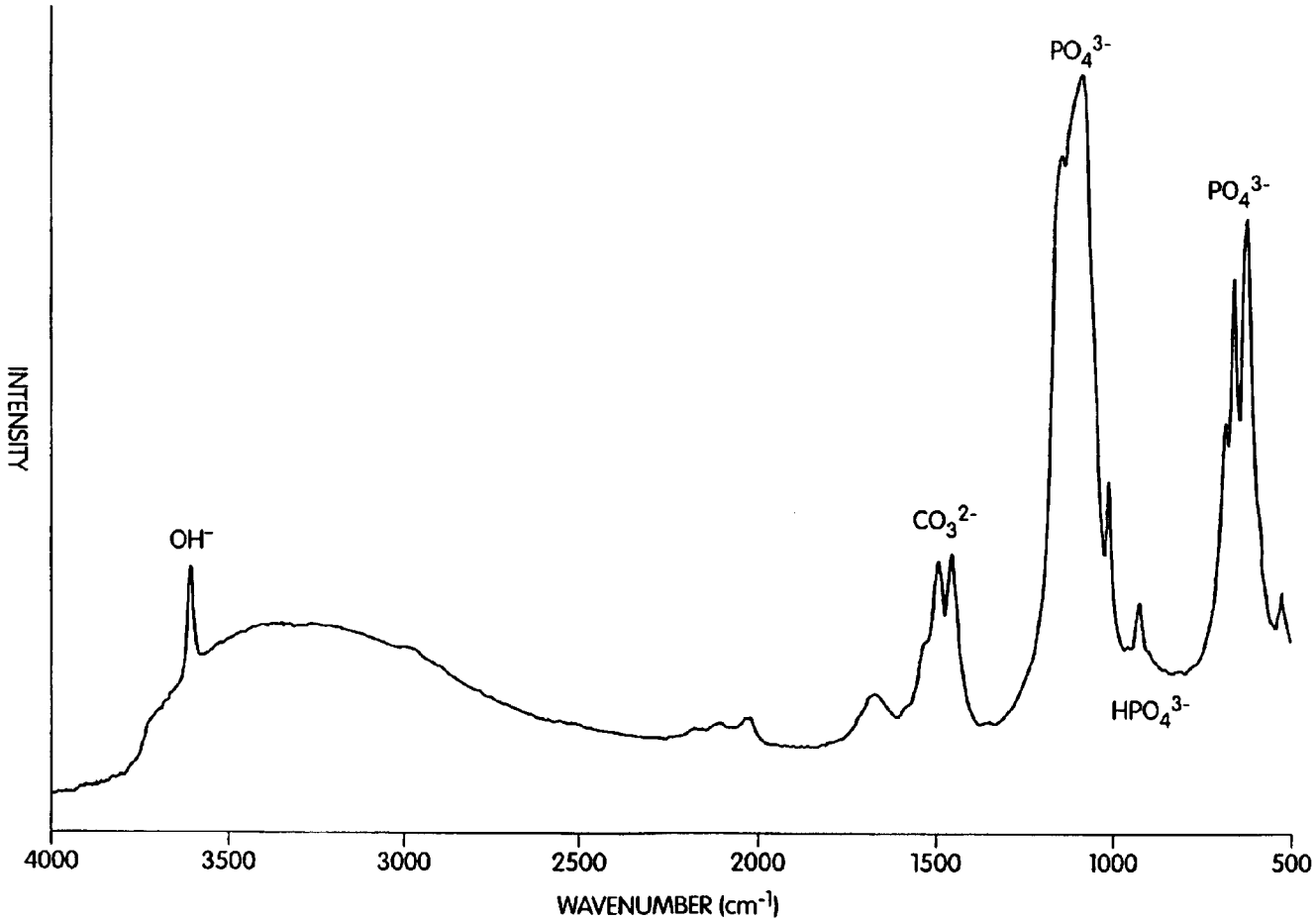
FIG. 6 is an PA-FTIR spectrum of the nanocrystalline hydroxyapatite sample for which the XRD pattern is provided in FIG. 5.

Thus, a superior hydroxyapatite would require excellent compositional homogeneity and could be subjected to a high temperature without decomposition, facilitating densification and maintaining mechanical integrity, and this is provided in accordance with the invention. FIGS. 3 and 4 illustrate the effect of sintering temperature on the XRD patterns of nano-hydroxyapatite powder and a comparative example of conventional hydroxyapatite powder (Aldrich), respectively.

Trial 2 nanocrystalline compact showed only hydroxyapatite peaks with no secondary β-TCP and CaO phases up to 1300° C. On the other hand, the XRD results showed that the conventional (Aldrich) compact sintered at 1000° C. has decomposed significantly to β-TCP with some CaO. By 1300° C., the main component was β-TCP with some CaO contained in the β-TCP matrix. Whereas the comparative compact began to transform to β-TCP by 1000° C., the nanocrystalline compact was found to be resistant to decomposition even at 1300° C.

EXAMPLE 4

Determination of Optimal Conditions-Grinding Method

The size of particle agglomerates can be reduced by techniques such as wet grinding. Smaller agglomerates allow for ceramic densification at lower sintering temperatures. By using a wet grinding technique, that is grinding the as-synthesized wet gel in a heated mortar until a fine powder is obtained, the size of the agglomerates can be reduced. If the gel is left to dry, capillary pressure begins to build up between the particles as the solvent between the particles is evaporated, squeezing the particles together to form large agglomerates. By wet grinding, the agglomerates are continually broken apart as more surface area is exposed. It is expected that wet ground powder has a higher surface area, and higher green and sintered densities than a dried gel. The green crystallite sizes would be expected to be similar given that the precipitation conditions are identical. The synthesis conditions of the calcined hydroxyapatite powders used to determine the effect of wet grinding are presented in Table 3. XRD crystallite size, BET surface area, green density and bulk density after sintering at 1100° C. are presented in Table 4.

TABLE 3

Effect of Grinding Method: Synthesis Conditions

| Trial | Aging Time (hr) | Rxn/Aging Temp (° C.) | $Ca(NO_3)_2$ Addition Rate (ml/min) | Grinding Method | CaN Concentration (M) | Amount (ml) | NHP Concentration (M) | Amount (ml) | $NH_4OH$ Amount (ml) |
|---|---|---|---|---|---|---|---|---|---|
| 1 | 12 | 25 | 15 | Dry | 0.500 | 300 | 0.300 | 300 | 30 |
| 2 | 12 | 25 | 15 | Wet | 0.500 | 300 | 0.300 | 300 | 30 |

TABLE 4

Effect of Grinding Method: Results

| Trial | XRD Crystallite Size (nm) | BET Surface Area ($m^2/g$) | Green Density (g/cc) | % Theoretical Sintered Bulk Density |
|---|---|---|---|---|
| 1 | 42 | 85.6 | 1.31 | 83.0 |
| 2 | 40 | 107.5 | 1.68 | 94.7 |

Results in Table 4 clearly confirm that wet grinding strongly affect the agglomerate size. The wet ground hydroxyapatite powders possess higher surface area, green density and sintered bulk densities than the dry ground powders. These results suggest that by grinding the gel while it is still wet, agglomerates size can be reduced thereby enhancing densification. Furthermore, wet grinding the gel does not affect the crystallinity of the material as shown by the XRD patterns of Trials 1 and 2. The wet and dry ground materials had a similar hydroxyapatite crystallite size. The PA-FTIR spectra showed the presence of $OH^-$, $H_2O$, and $PO_4^{3-}$ as well as $HPO_4^{2-}$ and a minor $CO_3^{2-}$ peak. Since wet grinding did not affect the crystallinity of the material but did significantly reduce agglomeration, it should be utilized in the processing of the hydroxyapatite precursor gel.

EXAMPLE 5

Determination of Optimal Conditions—Reaction and Aging Temperature

By altering the temperature of the precipitation reaction and the aging process, the crystal nucleation and growth can be controlled. By precipitating at low temperatures, crystal growth can be minimized resulting in finer crystals. The effect of processing temperature on XRD crystallite size, BET surface area, green density, and bulk density after sintering at 1100° C. were investigated in our study (see Tables 5 and 6).

TABLE 6

Effect of Reaction and Aging Temperatures: Results

| Trial | XRD Crystallite Size (nm) | BET Surface Area ($m^2/g$) | Green Density (g/cc) | % Theoretical Sintered Bulk Density |
|---|---|---|---|---|
| 3 | 47 | 63.0 | 1.50 | 92.2 |
| 2 | 40 | 107.5 | 1.68 | 94.7 |
| 4 | >100 | 61.09 | 1.50 | 83.8 |

As shown in Table 6, the calcined powders reacted and aged at 70° C. had larger crystallites than the powders reacted and aged at room temperature and 0° C. Since room temperature processing readily yields high green and sintered densities, 25° C. is the preferred reaction and aging temperature for the chemical precipitation of hydroxyapatite.

EXAMPLE 6

Effect of Aging Time

The crystallinity and structural development of hydroxyapatite can be affected by varying the aging time. By increasing the aging time, the hydroxyapatite precipitate undergoes recrystallization. As a result, occluded impurities are removed and crystal strain is reduced as free energy of the crystal decreases, while the crystal structure becomes perfected and the exposed area is decreased. Needle-like and rod-like structures redissolve and are recrystallized in more orderly morphologies such as spheres with the shapes of the primary particles approaching a homogeneous distribution. This phenomena can be also accompanied with a decrease in surface area. Furthermore, longer aging times ensure that the reagents are fully reacted and precipitate out of the solution. The synthesis conditions of the hydroxyapatite gels used to determine the effect of aging time are presented in Table 7.

TABLE 5

Effect of Reaction and Aging Temperatures: Synthesis Conditions

| Trial | Aging Time (hr) | Rxn/Aging Temp (° C.) | $Ca(NO_3)_2$ Addition Rate (ml/min) | Grinding Method | CaN Concentration (M) | Amount (ml) | NHP Concentration (M) | Amount (ml) | $NH_4OH$ Amount (ml) |
|---|---|---|---|---|---|---|---|---|---|
| 3 | 12 | 0 | 15 | Wet | 0.500 | 300 | 0.300 | 300 | 30 |
| 2 | 12 | 25 | 15 | Wet | 0.500 | 300 | 0.300 | 300 | 30 |
| 4 | 12 | 70 | 15 | Wet | 0.500 | 300 | 0.300 | 300 | 30 |

TABLE 7

Effect of Aging Time: Synthesis Conditions

| Trial | Aging Time (hr) | Rxn/Aging Temp (° C.) | $Ca(NO_3)_2$ Addition Rate (ml/min) | Grinding Method | CaN Concentration (m) | Amount (ml) | NHP Concentration (M) | Amount (ml) | $NH_4OH$ Amount (ml) |
|---|---|---|---|---|---|---|---|---|---|
| 5 | 12 | 25 | 2 | Wet | 0.500 | 300 | 0.300 | 300 | 30 |
| 6 | 100 | 25 | 2 | Wet | 0.500 | 300 | 0.300 | 300 | 30 |
| 7 | 12 | 25 | 3 | Wet | 0.167 | 900 | 0.100 | 900 | 90 |
| 8 | 100 | 25 | 3 | Wet | 0.167 | 900 | 0.100 | 900 | 90 |

TABLE 8

Effect of Aging Time: Results

| Trial | XRD Crystallite Size (nm) | BET Surface Area ($m^2/g$) | Green Density (g/cc) | % Theoretical Sintered Bulk Density |
|---|---|---|---|---|
| 5 | 44 | 58.52 | 1.31 | 82.6 |
| 6 | 41 | 65.68 | 1.70 | 80.4 |
| 7 | 45 | 63.57 | 1.43 | 87.7 |
| 8 | 33 | 89.71 | 1.88 | 95.3 |

The XRD patterns of Trials 5, 6, 7, and 8 agree with the JCPDS hydroxyapatite file (9-0432), and no other phases were observed. Trial 8 possessed a smaller XRD crystallite size than Trials 7 while similar grain sizes were noted for Trials 5 and 6. These results indicate that hydroxyapatite aged for 100 hours had a noticeably smaller average crystallite size than hydroxyapatite aged for 12 hours in hydroxyapatite prepared with the lower precursor concentration. Although FTIR spectra of Trials 5, 6, 7, and 8 possessed peaks characteristic of hydroxyapatite, the $HPO_4^{2-}$ peak at 875 $cm^{-1}$ and the peaks of $PO_4^{3-}$ at 1030-1090 $cm^{-1}$ and 560-600 $cm^{-1}$ were reduced in intensity and were broadened for the sample aged for 100 hours. The XRD patterns and the FTIR spectra indicated that the hydroxyapatite aged for 100 hours underwent significant dissolution and reprecipitation so that the crystallite size of the reprecipitated hydroxyapatite was smaller than that of the originally precipitated hydroxyapatite. Alternatively, amorphous calcium phosphate may have nucleated into small crystallites during long aging times reducing the average crystallite size.

Significant differences in the effect of aging time are observed for the hydroxyapatite synthesized using high and low precursor concentrations. In both cases, an increase in surface area is observed as aging time is increased, though a decrease in surface area is expected with longer aging times as predicted by Ostwald ripening. Instead of an Ostwald ripening phenomenon, there is a conversion from a low surface area amorphous calcium phosphate to a higher surface area crystalline hydroxyapatite; this interpretation is consistent with the decrease in XRD crystallite size as aging time is increased. The hydroxyapatite synthesized using 0.500 M $Ca(NO_3)_2$ and 0.300 M $(NH_4)_2HPO_4$ precursor concentrations aged for 12 hours (Trial 5) resulted in a higher sintered density than that aged for 100 hours (Trial 6). However, for hydroxyapatite synthesized using 0.167 M $Ca(NO_3)_2$ and 0.100 M $(NH_4)_2HPO_4$ precursor concentrations, aging for 100 hours (Trial 8) resulted in a higher sintered density than aging for 12 hours (Trial 7). These results suggest that particle morphology of the originally precipitated hydroxyapatite synthesized at high precursor concentrations (Trial 5) favors densification, while the particle morphology of the reprecipitated hydroxyapatite synthesized at low precursor concentrations (Trial 8) favors densification.

EXAMPLE 7

Effect of $NH_4OH$ Concentration pH can affect chemical precipitation by altering the solubility of the precipitate; the solubility of hydroxyapatite decreases as pH increases. As a result, nucleation would be favored decreasing crystallite size. Furthermore, different pH's affect agglomeration by inducing a surface charge on the particles in solution. Similar surface charges in the solution of the particles repel each other reducing agglomeration in the solution. However, the same polar solvents that prevented agglomeration during precipitation introduce surface hydroxyl groups onto ceramic particles during the drying process. As the ceramic gel dries, the surface hydroxyl groups promote agglomeration of particles. It is therefore desirable to use a nonpolar solvent, to wash the gel in order to remove the surface hydroxyl groups. Finally, the different pHs during the chemical precipitation are expected to affect crystal morphology, and the morphology becomes increasingly rod-like*, or spherical to needle-like,* with increasing pH*, for example to aspect ratios ranging from about 2.3:1 to 5.9:1.*Tanahashi et al. reported that the solution pH greatly influenced the growth rate and morphology of hydroxyapatite and that fibrous hydroxyapatite could be prepared at high pH. Hydroxyapatite synthesized through hydrothermal treatment at a pH of 11 to 12 also resulted in nanometer-sized rod-like crystals. However, the addition of glycerin during the synthesis confounded the relationship between high pH and the synthesis of rod-like hydroxyapatite, with the effect of additives on the synthesis of rod-like hydroxyapatite. The synthesis conditions of the calcined hydroxyapatite powders used to determine the effect of $NH_4OH$ are presented in Table 9.

TABLE 9

Effect of $NH_4OH$ Concentration: Synthesis Conditions

| Trial | Aging Time (hr) | Rxn/Aging Temp (° C.) | $Ca(NO_3)_2$ Addition Rate (ml/min) | Grinding Method | CaN Concentration (M) | Amount (ml) | NHP Concentration (M) | Amount (ml) | $NH_4OH$ Amount (ml) |
|---|---|---|---|---|---|---|---|---|---|
| 9 | 12 | 25 | 2 | Wet | 0.500 | 300 | 0.300 | 300 | 10 |
| 5 | 12 | 25 | 2 | Wet | 0.500 | 300 | 0.300 | 300 | 30 |
| 10 | 12 | 25 | 2 | Wet | 0.500 | 300 | 0.300 | 300 | 100 |
| 11 | 100 | 25 | 3 | Wet | 0.167 | 900 | 0.100 | 900 | 30 |
| 12 | 100 | 25 | 3 | Wet | 0.167 | 900 | 0.100 | 900 | 90 |
| 13 | 100 | 25 | 3 | Wet | 0.167 | 900 | 0.100 | 900 | 300 |

TABLE 10

Effect of $NH_4OH$ Concentration: Results

| Trial | XRD Crystallite Size (nm) | BET Surface Area ($m^2/g$) | Green Density (g/cc) | % Theoretical Sintered Bulk Density |
|---|---|---|---|---|
| 9 | 50 | 72.58 | 1.59 | 94.3 |
| 5 | 44 | 58.52 | 1.31 | 82.6 |
| 10 | 52 | 59.30 | 1.68 | 81.0 |
| 11 | 40 | 72.16 | 1.58 | 87.3 |
| 12 | 33 | 89.71 | 1.88 | 95.3 |
| 13 | Not HAP | Not HAP | Not HAP | Not HAP |

The XRD patterns show that all of the calcined hydroxyapatite samples, except for Trial 13, have good crystallinity and a pure hydroxyapatite phase. The peaks of the FTIR spectra were also consistent with hydroxyapatite. Trials 9, 5, and 10 correspond to 10 ml, 30 ml, and 100 ml of $NH_4OH$ at high precursor concentrations. The XRD results of Trials 9 and 5 suggest that the addition of more $NH_4OH$ gives rise to smaller XRD crystallites, which is consistent with the effect of increased pH which decreases solubility, favoring nucleation. However, the XRD crystallite size of Trial 10 is larger than Trial 5. This phenomenon can be explained by examining Trials 11,12, and 13 which correspond to 30 ml, 90 ml, and 300 ml of $NH_4OH$ at low precursor concentrations. The XRD crystallite sizes of Trials 11 and 12 decrease as pH is increased. Similar to Trial 10, Trial 13 deviates from the trend established by Trials 11 and 12. Instead of the anticipated further decrease in XRD crystallite size, as-synthesized Trial 13 is not hydroxyapatite but a combination of monetite ($CaHPO_4$) and brushite ($CaHPO_4.2H_2O$) Trial 10 may occur in a similar metastable state as Trial 13, though not as pronounced because of its shorter aging time and higher precursor concentrations. Thus, the possible presence of monetite and brushite during the synthesis of Trial 10 may give rise to the deviation in the crystallite size. Furthermore, samples prepared under similar conditions as Trial 13 have resulted in hydroxyapatite, confirming the metastability of this region.

Trial 9, the hydroxyapatite derived with 10 ml of $NH_4OH$, resulted in the highest surface area and the highest % theoretical sintered bulk density under a high precursor concentration synthesis. A low pH at high precursor concentrations produces a particle morphology and distribution favorable towards densification since the addition of $NH_4OH$ is known to affect particle morphology. Conversely, at low precursor concentrations, the highest surface area and highest % theoretical sintered bulk density occurred at an intermediate pH, indicating that this amount of $NH_4OH$ resulted in a particle morphology and distribution favorable toward densification.

EXAMPLE 8

Effect of Addition Rate

By varying the precursor addition rate, nucleation and crystal growth rates can be controlled. Rapid addition of precursors results in localized high concentrations of precursors, exceeding the solubility of hydroxyapatite in those regions, which favors nucleation and formation of small particles. However, rapid addition is also expected to result in a nonuniform particle morphology and distribution. Conversely, slow addition of precursors results in a more homogenous mixture of reactants favoring crystal growth and formation of larger particles. Furthermore, slow addition of precursors is anticipated to result in a uniform particle morphology and distribution. Thus, relatively few nuclei will be formed by adding $Ca(NO_3)_2$ slowly; crystal growth removes the precursors as fast as it is added. Adding $Ca(NO_3)_2$ quickly yields more and smaller particles. The synthesis conditions of the experiment investigating the effect of addition rate are presented in Table 11.

TABLE 11

Effect of Addition Rate: Synthesis Conditions

| Trial | Aging Time (hr) | Rzn/Aging Temp (° C.) | $Ca(NO_3)_2$ Addition Rate (ml/min) | Grinding Method | CaN Concentration (M) | Amount (ml) | NHP Concentration (M) | Amount (ml) | $NH_4OH$ Amount (ml) |
|---|---|---|---|---|---|---|---|---|---|
| 5 | 12 | 25 | 2 | Wet | 0.500 | 300 | 0.300 | 300 | 10 |
| 6 | 12 | 25 | 15 | Wet | 0.500 | 300 | 0.300 | 300 | 10 |
| 7 | 100 | 25 | 3 | Wet | 0.167 | 900 | 0.100 | 900 | 90 |
| 8 | 100 | 25 | 48 | Wet | 0.167 | 900 | 0.100 | 900 | 90 |

TABLE 12

Effect of Addition Rate: Results

| Trial | XRD Crystallite Size (nm) | BET Surface Area ($m^2/g$) | Green Density (g/cc) | % Theoretical Sintered Bulk Density |
|---|---|---|---|---|
| 5 | 67 | 73.58 | 1.59 | 94.3 |
| 6 | 54 | 65.20 | 1.52 | 91.8 |
| 7 | 33 | 89.71 | 1.74 | 95.6 |
| 8 | 31 | 65.35 | 1.91 | 95.3 |

The XRD patterns of Trials 9, 14, 15, and 12 corresponded to the JCPDS hydroxyapatite file (9-0432) and no other phases were found. All FTIR spectra possess peaks characteristic of nanocrystalline hydroxyapatite. Trials 9 and 15 possessed a larger XRD crystallite size and a higher BET surface area than Trials 14 and 12, respectively, and gave rise to higher sintered densities. The larger XRD crystallite sizes of Trials 9 and 12 compared to 14 and 12 suggest that a slower addition rate favors crystal growth, as anticipated. In addition, by using a slow addition to obtain a more uniform particle morphology and distribution, the final sintered bulk densities were enhanced. These effects were significant for Trials 9 and 14, but addition rate did not play a dominant role in Trials 15 and 12. The lesser role of addition rate at low precursor concentrations can be attributed to the difference in molar flow rates. The difference in molar rates between Trials 15 and 12 is $7.5\times10^{-3}$ moles/min whereas the difference in molar flow rates between Trials 9 and 14 is $7.4\times10^{-2}$ moles/min. These results confirm that crystallite size depends on the rate of addition with slower rates of addition resulting in larger crystallites, but to observe this effect at low precursor concentrations, a much higher flow rate should be used. To obtain a densified nanocrystalline hydroxyapatite ceramic, $Ca(NO_3)_2$ should be added slowly to the basic $(NH_4)_2HPO_4$ solution.

EXAMPLE 9

Effect of Precursor Concentration

By varying the precursor concentration, the synthesis of nanocrystalline hydroxyapatite can be further controlled by affecting the kinetics of hydroxyapatite synthesis. By reducing the precursor concentration, the kinetics of the reaction are slowed. The synthesis conditions of the hydroxyapatite gels used to determine the effect of precursor concentration are presented in Table 13.

TABLE 14

Effect of Precursor Concentration: Results

| Trial | XRD Crystallite Size (nm) | BET Surface Area ($m^2/g$) | Green Density (g/cc) | % Theoretical Sintered Bulk Density |
|---|---|---|---|---|
| 9 | 67 | 73.58 | 1.59 | 94.3 |
| 16 | 46 | | 1.82 | 85.1 |
| 17 | 41 | 65.68 | 1.70 | 80.1 |
| 15 | 33 | 89.71 | 1.74 | 95.6 |

The XRD patterns of Trials 9, 17, and 15 correspond to hydroxyapatite while the XRD pattern of Trial 16 corresponds to monetite ($CaPO_3OH$). The FTIR spectra of Trials 9, 17, and 15 also showed the characteristic hydroxyapatite nanocrystalline peaks. By reducing the precursor concentration in Trial 9 to the precursor concentration of Trial 16, hydroxyapatite synthesis enters an intermediate state where monetite is the product. In Table 8, "Effect of Aging Time," Trials 7 and 8 were both found to be hydroxyapatite regardless of aging time, but unlike Trial 16, Trials 7 and 8 were synthesized under a higher pH. Tables 15 and 16 present the synthesis conditions and results proving that Trial 16 is an intermediate state, observable because of the shorter aging time, low precursor concentration and low pH; under the same conditions as Trial 16, except with longer aging times, Trial 11 was determined to be hydroxyapatite. Thus, the effect of lowering precursor concentration at the synthesis conditions of Trials 9 and 16 is to slow the kinetics of the reaction.

TABLE 13

Effect of Precursor Concentration: Synthesis Conditions

| Trial | Aging Time (hr) | Rxn/Aging Temp (° C.) | $Ca(NO_3)_2$ Addition Rate (ml/min) | Grinding Method | CaN Concentration (M) | Amount (ml) | NHP Concentration (M) | Amount (ml) | $NH_4OH$ Amount (ml) |
|---|---|---|---|---|---|---|---|---|---|
| 9 | 12 | 25 | 2 | Wet | 0.500 | 300 | 0.300 | 300 | 10 |
| 16 | 12 | 25 | 3 | Wet | 0.167 | 900 | 0.100 | 900 | 30 |
| 17 | 100 | 25 | 2 | Wet | 0.500 | 300 | 0.300 | 300 | 30 |
| 15 | 100 | 25 | 3 | Wet | 0.167 | 900 | 0.100 | 900 | 90 |

TABLE 15

Effect of Aging Time on Trial 16: Synthesis Conditions

| Trial | Aging Time (hr) | Rxn/Aging Temp (° C.) | $Ca(NO_3)_2$ Addition Rate (ml/min) | Grinding Method | CaN Concentration (m) | Amount (ml) | NHP Concentration (m) | Amount (m1) | $NH_4OH$ Amount (ml) |
|---|---|---|---|---|---|---|---|---|---|
| 16 | 12 | 25 | 3 | Wet | 0.167 | 900 | 0.100 | 900 | 30 |
| 11 | 100 | 25 | 3 | Wet | 0.167 | 900 | 0.100 | 900 | 30 |

TABLE 16

Effect of Aging Time on Trial 16: Results

| Trial | XRD Crystallite Size (nm) | BET Surface Area ($m^2/g$) | Green Density (g/cc) | % Theoretical Sintered Bulk Density |
|---|---|---|---|---|
| 16 | Not HAP | Not HAP | Not HAP | Not HAP |
| 11 | 40 | 72.16 | 1.58 | 87.3 |

At longer aging times and higher pH (Trials 17 and 15), a kinetic effect is also observed. Because of the low precursor concentration, the rate of reaction is expected to be slower for Trial 15 than Trial 17 as confirmed by the smaller XRD crystallite size of Trial 15. Furthermore, the slower kinetics of Trial 15 compared to Trial 17 resulted in a higher surface area, and a particle morphology and size distribution favoring densification.

Two synthesis conditions, Trial 9 and 15, were determined to give rise to the optimal hydroxyapatite powders as assessed by % theoretical sintered bulk density. Trial 15 possessed the highest pressurelessly sintered bulk density of all trials investigated. The 95.6% theoretical sintered bulk density was obtained using a low precursor concentration, 100 hour aging time, an aging temperature of 25° C., 3 ml/min $Ca(NO_3)_2$ addition rate, 90 ml of $NH_4OH$, and wet grinding. A high theoretical density of 94.3% was obtained using the synthesis conditions of Trial 9: high precursor concentration, 12 hour aging time, an aging temperature of 25° C., 2 ml/min addition rate, 10 ml of $NH_4OH$, and wet grinding. Thus, optimal conditions were determined for the precursor concentrations investigated.

SUMMARY OF EXAMPLES 1-9

Nanocrystalline hydroxyapatite was synthesized successfully by chemical precipitation. The effects of $NH_4OH$ amount, aging time, aging temperature, grinding method, precursor concentration, and $Ca(NO_3)_2$ addition rate on the crystallite size, agglomeration, morphology, crystallinity and the molecular structure were examined. By identifying the important processing parameters and the method by which they can be controlled, the crystallite size can be reduced to enhance the mechanical properties of bulk hydroxyapatite. Furthermore, using the parameters to reduce agglomeration, to control the particle morphology and size distribution, and to control the chemical reactivity of the particles, full densification can be achieved at lower sintering temperatures. The XRD patterns of the nano-hydroxyapatite precursor gel were in good agreement with the JCPDS hydroxyapatite file (9-432); the peaks were substantially broadened due to the nanocrystalline nature of hydroxyapatite. The grinding method affected the surface area and the state of agglomeration with wet grinding being favored. Reaction and aging temperatures during precipitation affected the crystal growth rate with room temperature favored. Aging time affected the conversion of the precipitate into a crystalline hydroxyapatite, the crystallite size, and the particle morphology and size distribution. Short aging times were preferred by high precursor concentrations and long aging times were preferred by low precursor concentrations. Amount of $NH_4OH$ affected the solubility of hydroxyapatite and the particle morphology and size distribution. Low $NH_4OH$ amounts were preferred at high precursor concentrations favored low $NH_4OH$ amounts while intermediate $NH_4OH$ amounts were preferred at low precursor concentrations. Precursor addition rate affected the nucleation and crystal growth rates and particle morphology. Slow addition rates were preferred at both high and low precursor concentrations. Precursor concentration affected the rate of reaction of hydroxyapatite. Optimal conditions were determined for both precursor concentrations. The nano-hydroxyapatite precursor gel heat treated at 550° C. gave an ultrafine grain size of 40 nm by TEM observation. This high-purity nano-hydroxyapatite also had higher B.E.T. surface areas than samples heat treated to 700° C. or 900° C. and was used to prepare compacts for pressureless sintering. The nano-hydroxyapatite compact had superior sinterability when compared to conventional hydroxyapatite. The highly densified hydroxyapatite was obtained by pressureless sintering at 1100° C. Also, the dense compacts derived from nanocrystalline hydroxyapatite demonstrated excellent resistance to high-temperature decomposition, compared to the conventional hydroxyapatite. This should give rise to superior properties in bioceramic applications. The nano-hydroxyapatite synthesized in this study was resistant to thermal decomposition into β-TCP and CaO up to 1300° C.

EXAMPLE 10

Colloidal and Hot Pressing of Nanocrystalline Hydroxyapatite

By only controlling the synthesis parameters without any subsequent powder processing, 96% theoretical bulk density was obtained, indicating the superiority of this nanocrystalline hydroxyapatite powder. To further illustrate the improvements of the nanocrystalline hydroxyapatite and its processing over the conventional hydroxyapatite and conventional processing and to exceed the 96% theoretical bulk density obtained from pressureless sintering, the nanocrystalline powders were densified by colloidal and hot pressing.

Table 17 presents the synthesis conditions of the hot pressed powders, and Table 18 illustrates the effect of hot pressing on the sintered densities and compares the densities obtained from hot pressing to those obtained from pressureless sintering at 1100° C. All powders were hot pressed at a pressure of 54 MPa and at a ramp rate of 10° C./min and with a dwell time of 30 minutes at 1100° C. After hot pressing, the pellets were polished with 600 grit and 800 grit SiC. Densities were measured by Archimedes' method in water.

TABLE 17

Effect of Hot Pressing: Synthesis Conditions

| Trial | Aging Time (hr) | Rxn/Aging Temp (° C.) | $Ca(NO_3)_2$ Addition Rate (ml/min) | Grinding Method | CaN Concentration (M) | Amount (ml) | NHP Concentration (M) | Amount (ml) | $NH_4OH$ Amount (ml) |
|---|---|---|---|---|---|---|---|---|---|
| 18 | 12 | 0 | 2 | Wet | 0.500 | 300 | 0.300 | 300 | 30 |
| 9 | 12 | 25 | 2 | Wet | 0.500 | 300 | 0.300 | 300 | 10 |
| 19 | 12 | 25 | 13 | Wet | 0.167 | 900 | 0.100 | 900 | 90 |

TABLE 18

Effect of Hot Pressing: Results

| Trial | XRD Crystallite Size (nm) | BET Surface Area ($m^2/g$) | Green Density (g/cc) | % Theoretical Bulk Density by Pressureless Sintering at 1100° C. | % Theoretical Bulk Density by Hot Pressing at 1000° C. |
|---|---|---|---|---|---|
| 18 | 36 | 53.70 | 1.56 | 67.7 | 3.05 g/cc |
| 9 | 67 | 72.58 | 1.59 | 94.3 | 98.5 |
| 19 | 38 | 70.77 | 1.49 | 91.1 | 99.0 |

From the results presented in Table 18, hot pressing is observed to have a dramatic impact on the sintering of the hydroxyapatite powder. Hot pressing increased the % theoretical bulk density of the powder from Trial 9, one of the optimal conditions determined in the previous section, to 98.5% and enabled Trial 19 to achieve 99% theoretical density. The pellets of Trial 9 and 19 possessed a glassy finish and were slightly translucent. The β-TCP decomposition products, barely detectable by XRD, were found in the XRD patterns of the hot pressed powders from Trials 9 and 19. Furthermore, the grain sizes of the sintered pellets were found to be less than 225 nm by SEM, indicating that an ultrafine microstructure was present after the sintering process. Remarkably, even with a powder with poor pressureless sintering characteristics such as that of Trial 18, the bulk density can be increased from 2.14 g/cc to 3.05 g/cc through hot pressing. Though this sample decomposed significantly into β-TCP, this pellet was pore-free as indicated by the transparency of the pellet. The operating conditions presented for hot pressing provide an upper limit for sintering temperature and a lower limit for the applied pressure because of the slight decomposition detected in the XRD patterns. Observations indicate that densification stops before 1000° C., and that 900° C. or 800° C. may be the preferred sintering temperature. By hot pressing, the sintering temperature can be reduced by 200° C. or 300° C. Increasing the applied pressure is also anticipated to facilitates the sintering process. The most dramatic results from hot pressing are associated with a less crystalline and a more amorphous hydroxyapatite starting powder. Hot pressing seems to favor powders synthesized under either low temperature or low precursor concentration conditions. The results from hot pressing are a further demonstration of the superiority of the nanocrystalline hydroxyapatite powder; without any special powder processing, full densification of hydroxyapatite can be achieved.

Colloidal Pressing

The sample (Trial 20) prepared by colloidal pressing was synthesized under the similar conditions as Trial 15. The as-synthesized hydroxyapatite gel, instead of rinsing and centrifuging with ethanol in the last two washing steps, was washed with water. A slurry was prepared, and this slurry was colloidally pressed. After careful drying, the pellet was CIPed to 300 MPa and sintered to 1100° C. for 2 hours at 5° C./min. A highly translucent pellet was obtained with a 95.8% theoretical density. However, slight decomposition was detected in the XRD patterns. These data do strongly suggest that the hydroxyapatite prepared by the method described in previous section is well suited to colloidal pressing as indicated by the translucent pellet. A mild hydrothermal treatment of the precipitate prior to colloidal pressing may improve sintering by increasing the crystallinity of the material and by reducing the reactivity of the as-synthesized gel; the hydroxyapatite phase will be more stable and decomposition will be reduced. Furthermore, by controlling the pH and ionic strength of the slurry (e.g. by the addition of $NH_4NO_3$), the state of agglomeration and particle morphology can be controlled to enhance densification.

EXAMPLE 11

Synthesis and Characterization of Hydroxyapatite-Zirconia Composites

A composite including an apatite and a structural additive was prepared, with the additive selected to enhance the mechanical properties. To further strengthen hydroxyapatite and to maintain the nanocrystallinity after sintering, the addition of a secondary component is proposed. Many types of hydroxyapatite composites have been developed to take advantage of both the properties of hydroxyapatite and of the secondary phases. Hydroxyapatite-polymer composites have been developed to improve upon the mechanical reliability of conventional hydroxyapatite. Hydroxyapatite has also been used as the reinforcing phase in glass-hydroxyapatite composites. Hydroxyapatite composites formed with another secondary ceramic phase such as alumina or zirconia have been shown to significantly improve the mechanical properties of hydroxyapatite. The hydroxyapatite-alumina composites required complex processing such as glass encapsulated hot isostatic pressing. Significant improvements in mechanical properties were observed when vol % alumina in the composite increased above 50%. However, as the volume % of alumina is increased, the bioactivity of the composite decreases. The mechanical properties of the hydroxyapatite-zirconia composites are expected to match or exceed the hydroxyapatite-alumina composites while using a smaller volume % of zirconia. This is because zirconia has more mechanisms by which it can provide mechanical reinforcement than alumina. Zirconia dispersiods can toughen the hydroxyapatite matrix by a transformation toughening mechanism as well as crack deflection. By using nanocrystalline materials processing, the mechanical properties can be further enhanced. The zirconia dispersion can then be used to "pin" the hydroxyapatite grains suppressing grain growth during calcination and sintering to preserve nanometer-sized crystallites.

In trying to develop a composite with the optimal mechanical properties, the effects of the grain sizes of the hydroxyapatite and zirconia, dopant concentration, milling time, and milling intensity were investigated. Nanocrystalline hydroxyapatite and zirconia were synthesized by chemical precipitation. Through the previous studies on the synthesis and characterization of hydroxyapatite, the processing parameters can be controlled to obtain a specified grain size and particle morphology and sintered density.

Synthesis of Nanocrystalline Hydroxyapatite

Aqueous solutions of 0.300 M $(NH_4)_2HPO_4$ and 0.500 M $Ca(NO_3)_2$ were prepared so that the Ca:P ratio was 10:6 and were mixed with a magnetic stirrer. The pH of the $(NH_4)_2HPO_4$ aqueous solution was varied by adding 30 ml of concentrated $NH_4OH$. 300 ml of a 0.500 M solution of $Ca(NO_3)_2$ was added to 300 ml of 0.300 M aqueous $(NH_4)_2HPO_4$ at 10 ml/min. The combined solutions were magnetically stirred for 12 hours and aged at room temperature. The white precipitate was collected by filtration with a Buchner funnel and washed at least three times with distilled water with a decreasing concentration of $NH_2OH$ each time and finally with ethanol. The gel was air dried at room temperature for 24 hours and then dried in a 150° C. oven for 12 hours. The gel was then finely ground with an alumina mortar and pestle. The ground powders were then heat treated in air at 550° C. with a heating rate of 10° C./min, and a dwell time of 2 hours.

Synthesis of Nanocrystalline Zirconia

A 2.00 M $ZrOCl_2.8\ H_2O$ (3 mol % $Y_2O_3$) stock solution is prepared from reagent grade $ZrOCl_2.8\ H_2O$ and $Y_2O_3$ and deionized water. The stock solution is allowed to stir for 24 hours prior to use. 25 ml of the 2.00 M $ZrOCl_2.8\ H_2O$ (3 mol % $Y_2O_3$) is pipetted 225 ml of ethanol under constant stirring. This working solution is allowed to stir for 30 minutes. Next, a base solution is prepared by pipetting 100 ml of ammonium hydroxide into 250 ml of ethanol under constant stirring and by allowing the solution to stir for at least 15 minutes. The precipitation reaction occurs when the 0.200 M working solution is added to a base solution at 15 ml/min under constant stirring. The solution is allowed to stir and age for 24 hours. Next, the solution is centrifuged at 1500 rpm for 20 minutes and decanted. The resulting gel is redispersed in ethanol and centrifuged 4 more times under the same conditions to quench the reaction and to remove all the chloride ions. The gel is then ground with a pestle in a preheated mortar until a fine powder is obtained. This powder is allowed to dry in a 110° C. oven overnight. Finally, the powder is calcined at 550° C. for 2 hours with a ramp rate of 10° C./min.

Proof of Concept and Initial Studies

In these series of experiments, composites formed from conventional hydroxyapatite (Aldrich), conventional zirconia (Toso), nanocrystalline hydroxyapatite, and nanocrystalline zirconia heat treated at 550° C. were investigated. The composite was formed by dry milling the hydroxyapatite with 10 vol % of zirconia for 24 hours, CIPing at 300 MPa for 3 minutes, pressureless sintering for 2 hours in air at sintering temperatures of 1100° C., 1200° C., and 1300° C. This dry ball milling ensured good mixing and contact between the two components without the transformations that might occur by high-energy ball milling. The XRD patterns of the nanocrystalline $Y_2O_3$-doped $ZrO_2$ indicated the presence of zirconia as 12 nm crystallites. A PA-FTIR spectrum indicated the presence of Zr-O-Zr, $H_2O$ and ZrOH peaks. The calcined nanocrystalline $Y_2O_3$-doped $ZrO_2$ possessed a BET surface area of 140 $m^2/g$ and an average pore size of 9 nm. After calcination at 550° C., the nanocrystalline hydroxyapatite had a XRD crystallite size of 32 nm and a BET surface area of 66.8 $m^2/g$.

The XRD patterns of the sintered nano-hydroxyapatite/nano-zirconia composite indicated that the composite was thermally stable up to 1200° C., and that significant phase transformation of hydroxyapatite and zirconia into tricalcium phosphate and monoclinic zirconia, respectively, occurred at 1300° C. When comparing the sinterability of nano-hydroxyapatite and zirconia reinforced hydroxyapatite, the composite required a higher sintering temperature of 1200° C. to achieve full densification while the pure nano-hydroxyapatite required 1100° C. to achieve full densification. The nanocrystalline composite possessed better sinterability than any composite containing a conventional hydroxyapatite and/or $ZrO_2$ powder. By 1200° C., the nano-hydroxyapatite/nano-zirconia composite attained 98% theoretical density of hydroxyapatite while nano-hydroxyapatite/zirconia (Toso) achieved less than 70% theoretical density by 1300° C.

TEM micrographs indicated that there were no glassy phases at the grain boundaries showing that the nanocomposite achieved good densification without the precipitation of undesirable secondary phases. Zirconia grains were intragranularly dispersed within the hydroxyapatite matrix. With smaller grain sizes, a more mechanically robust material is obtained. The pure nanocrystalline hydroxyapatite possessed a compressive strength of 745 MPa while the conventional micron-sized hydroxyapatite possessed a compressive strength of 150 MPa. Further reinforcement of the nanocrystalline hydroxyapatite with a secondary dispersoid of nanocrystalline zirconia resulted in an even higher compressive strength of 1020 MPa. This improvement in compressive strength is believed to be due to the intragranular toughening of the nanocrystalline hydroxyapatite matrix by the nano-$ZrO_2$ dispersoids.

Another method for the synthesis of nanocrystalline hydroxyapatite yields an improved nanocomposite with an even higher compressive strength, a lower sintering temperature and greater thermal stability. The method of producing the composite uses ajar mill to disperse the zirconia into the hydroxyapatite. Recent experiments suggests that better mixing and contacting between the zirconia and hydroxyapatite can be achieved by co-precipitation, or by dispersing zirconia particles during either the chemical precipitation or the aging of the nanocrystalline hydroxyapatite.

The proof of concept and initial studies of the synthesis of hydroxyapatite/zirconia nanocomposite used an earlier method for the synthesis of nanocrystalline hydroxyapatite. By using the recently optimized method for the synthesis of nanocrystalline hydroxyapatite (Trial 9 or 15), an improved nanocomposite with an even higher compressive strength, a lower sintering temperature and greater thermal stability may be produced. The method of producing the composite reported above used a jar mill to disperse the zirconia into the hydroxyapatite. Recent experiments suggest that better mixing and contacting between the zirconia and hydroxyapatite can be achieved by dispersing zirconia particles during either the chemical precipitation or the aging of the nanocrystalline hydroxyapatite.

EXAMPLE 12

Synthesis and Characterization of Nanocrystalline Carbonate Hydroxyapatite

Since the mineral phase of human bone has recently been identified as carbonate apatite, not hydroxyapatite[7], a nanocrystalline carbonate apatite can be used as a reactive layer on a bioceramic to enhance bioactivity for bone growth on the surfaces of the implant. Because the poor mechanical properties of carbonate apatite prevent it from being used as a structural material, the focus of this work will be the synthesis and the characterization of nanocrystalline carbonate apatite powder. With the ability to synthesize a high surface area carbonate apatite powder, the bioactivity of artificial bone crystals can be controlled.

To further illustrate the versatility of the preparative technique developed for synthesis of hydroxyapatite, the chemical precipitation process in which nanocrystalline hydroxyapatite is synthesized was modified to derive nanocrystalline carbonate apatite, $Ca_{10}(PO_4)_6CO_3$ (Type A where the $CO_3^{2-}$ occupies the monovalent anionic ($OH^-$) sites) or $Ca_{10-x}(PO_4)_{6-2x}(CO_3)_{2x}(OH)_{2(1-x)}$ (Type B where the $CO_3^{2-}$ occupies the trivalent anionic ($PO_4^{3-}$) sites). Type A carbonate apatite is a well-defined class of compounds normally synthesized at elevated temperatures. In contrast, Type B carbonate apatite is a poorly defined class of compounds typically synthesized at low temperatures under aqueous conditions. Carbonate apatite can be generated by either saturating the reaction solution with carbon dioxide or by adding another carbonate source such as sodium bicarbonate or ammonium bicarbonate, followed by a hydrothermal treatment, in an attempt to stabilize the carbonate ion in the precipitate.

Synthesis of Nanocrystalline Carbonate Apatite

Aqueous solutions of 0.075 M to 0.300 M $(NH_4)_2HPO_4$ and 0.500 M $Ca(NO_3)_2$ were prepared so that the Ca:P ratio varied from 6.67 to 1.67 and were mixed with a magnetic stirrer. The pH of the $(NH_4)_2HPO_4$ aqueous solution was adjusted by adding 10 ml of concentrated $NH_4OH$. 300 ml of a 0.500 M solution of $Ca(NO_3)_2$ was added to 300 ml of 0.300 M aqueous $(NH_4)_2HPO_4$ at 3 ml/min. A gas stream composed of 5% CO, and 95% $N_2$ was bubbled through the precipitate immediately after addition or 6 hours after addition for 18 hours. Some trials were magnetically stirred for 100 hours and aged at room temperature, while others were aqueously aged for 50 hours followed by 50 hours of hydrothermal treatment at 180° C. The white precipitate was collected by centrifugation at 1500 rpm for 15 minutes. After decanting, the precipitate was redispersed in a solution of distilled water and $NH_4OH$ by magnetically stirring for 20 minutes; this procedure was repeated two more times with decreasing amounts of $NH_4OH$, and two times with ethanol. The gel was air dried at room temperature for 24 hours, and then dried in a 150° C. oven for an additional 24 hours. The gel was then finely ground with an alumina mortar and pestle. The ground powders were then heat treated in air at 550° C., 700° C. and 900° C. with a heating rate of 10° C./min, and a dwell time of 2 hours.

Proof of Concept and Initial Studies

The synthesis of hydroxyapatite is known to undergo an induction period. Prior to hydroxyapatite formation, the precipitate is thought to convert from an amorphous calcium phosphate to an octacalcium phosphate and then to hydroxyapatite. Furthermore, the induction period increases with increasing pH. By synthesizing the hydroxyapatite at a low pH, higher solubility of hydroxyapatite is anticipated to aid the incorporation of the carbonate ion. In this initial study, the effect of carbonate substitution during pre- and post-HAP formation, the effect of varying the Ca/P ratio, and the effect of aqueous aging versus hydrothermal treatment were examined. In all samples, a mixed phase of hydroxyapatite, Type A and Type B carbonate apatite was detected. Introducing $CO_2$ immediately after the addition of $Ca(NO_3)_2$ was found to minimize the formation of $CaCO_3$, as determined by the XRD patterns and FTIR spectra. If $CO_2$ was added 6 hours after $Ca(NO_3)_2$ addition was completed, significant $CaCO_3$ formed because more calcium cations were in solution as a result of the reprecipitation process, while calcium was bound in the precipitate immediately after $Ca(NO_3)_2$ addition. In both aqueous aging and hydrothermal treatment, $CaCO_3$ was detected in the XRD patterns when $[(NH_4)_2HPO_4]<0.224$ M. For aqueously aged samples, both Type A and Type B carbonate apatites were detected in FTIR spectra. 879 $cm^{-1}$ is assigned to Type A carbonate apatite, and 873 $cm^{-1}$ is assigned to Type B carbonate apatite. Type A is favored over Type B for aqueously aged samples when $[(NH_4)_2HPO_4]=0.3$ M. For this sample, the XRD crystallite size was determined to be 25 nm. This is considerably smaller than the XRD crystallite size determined from hydroxyapatite synthesis which strongly suggests that the presence of the carbonate ions restricts crystal growth. $CaCO_3$ became the dominant phase for aqueously aged samples when $[(NH_4)_2HPO_4]<0.224$ M. For hydrothermally aged samples, both Type A and Type B carbonate apatites were detected in the FTIR spectra but the relative intensity of the Type A and Type B peaks suggests that hydrothermal treatment is more selective towards Type A carbonate apatite formation. Hydrothermal treatment stabilized the apatite phase with $CaCO_3$ becoming the dominant phase when $[(NH_4)_2HPO_4]<0.075$ M. In a subsequent experiment, carbonate apatite was synthesized under the following conditions: (1) 300 ml 0.5 M $Ca(NO_3)_2$, (2) 300 ml 0.3 M $(NH_4)_2HPO_4$, (3) 10 ml $NH_4OH$, (4) 80° C. reaction and aging temperature, (5) 3 ml/min $Ca(NO_3)_2$, and (6) immediate introduction of $CO_2$ after $Ca(NO_3)_2$ was added at 3 ml/min. The XRD pattern was identified as an apatite, with the FTIR spectra detecting Type A and Type B with Type A slightly favored. The XRD crystallite size for this sample was 65 nm, also considerably smaller than sizes measured for hydroxyapatite synthesized at similar conditions. These results suggest that Type B will be favored when synthesized at temperatures below 25° C. Furthermore, the introduction of carbonate into the apatite structure may be more carefully controlled by using $NH_4HCO_3$ instead of $CO_{2(g)}$. The surface areas for nanocrystalline carbonate apatite is expected to be similar to or greater than the surface areas of nanocrystalline hydroxyapatite synthesized under similar conditions.

This example illustrates the versatility of the process developed for synthesizing nanocrystalline hydroxyapatite and the benefits of carefully controlling the process parameters. By introducing a carbonate source and controlling the processing parameters, a nanocrystalline carbonate apatite, both Type A and Type B, was synthesized. Through further refinement, Type A and Type B carbonate apatite can be selectively synthesized, and the degree of substitution of carbonate ions for the phosphate ions in Type B carbonate apatite can be controlled. Important parameters will be reaction and aging temperatures, carbonate source, method of carbonate introduction, precursor concentrations, aging time, and pH.

SUMMARY OF EXAMPLES

The above examples demonstrate superior processes and products resulting from densifications of nanocrystalline hydroxyapatite. The grain sizes of calcined samples varied from 30 nm to 100 nm depending how pH, aging time, reaction and aging temperature, $Ca(NO_3)_2$ addition rate, precursor concentration, and grinding method were controlled, while the grain sizes of conventional hydroxyapatite were on a micron scale. For example, the surface area of one sample of the invention after calcination at 550° C. is 159.5 $m^2/g$ while the conventional sample after calcination at 550° C. has a very small surface area of 5.4 $m^2/g$. The sample of the invention retained phase uniformity after calcination at 550° C., but the conventional sample began to transform into tricalcium phosphate at 550° C. with substantial conversion to tricalcium phosphate and calcia by 700° C. In a sample of the invention 96% of the theoretical density was obtained at a low sintering temperature of 1100° C. by pressureless sintering for nanocrystalline hydroxyapatite which was stable up to 1300° C. However, the conventional sample achieved only 70% of the theoretical density at 1200° C. with decomposition into tri-calcium phosphate. Furthermore, the densified conventional sample contained large pores and microcracks. Our nanocrystalline hydroxyapatite has high purity and phase homogeneity as well as superior sinterability compared to the conventionally prepared hydroxyapatite. When our nanocrystalline hydroxyapatite was sintered using either colloidal or hot pressing, 99% theoretical bulk density with a grain size of less than 250 nm can be obtained. Dense nanocrystalline hydroxyapatite compacts further possessed a compressive strength as high as 745 MPa, while the conventional micronsized hydroxyapatite compacts from a similar pressureless sintering treatment possessed a compressive strength of 150 MPa. Additionally, further reinforcement of the hydroxyapatite can be accomplished by introducing a secondary dispersoid such as zirconia which would greatly improve the toughness and chemical stability of hydroxyapatite by pinning the mobility of any intergranular and intragranular defects. A dense composite of nanocrystalline hydroxyapatite and 10 wt % nanocrystalline 3 mol % $Y_2O_3$-doped $ZrO_2$ possessed an even higher compressive strength of 1020 MPa. With more complete characterization, the densified nanocrystalline hydroxyapatite and hydroxyapatite-zirconia composites can easily be developed into dental and orthopedic weight-bearing implants. Furthermore, the processing of nanocrystalline hydroxyapatite can be adapted to synthesize a nanocrystalline carbonate apatite illustrating the versatility of our process. This process can also be used to selectively synthesize Type A and Type B carbonate apatite as well as to control the degree of substitution of the carbonate ion into the apatite structure.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed is:

[1. A composition, comprising particulate apatite having an average apatite crystal size of less than 100 nm, wherein the crystal is spherical.]

[2. The composition of claim 1 comprising particulate apatite having an average apatite crystal size of less than 50 nm.]

[3. The composition of claim 1 comprising particulate apatite having an average apatite crystal size of less than 30 nm.]

[4. The composition of claim 1 comprising particulate apatite having an average apatite crystal size of less than 20 nm.]

[5. A composition as in claim 1 wherein the particulate apatite is densified.]

[6. The composition of claim 1 comprising apatite having an average particle size of less than 1 μm.]

[7. The composition of claim 1 comprising apatite having an average particle size of less than 0.5 μm.]

[8. The composition of claim 1 comprising apatite having an average particle size of less than 0.25 μm.]

[9. A composition comprising particulate apatite having a surface area of at least 40 $m^2/g$ and a spherical crystal.]

[10. The composition of claim 7 comprising particulate apatite having a surface area of at least 100 $m^2/g$.]

[11. The composition of claim 9 comprising particulate apatite having a surface area of at least 150 $m^2/g$.]

[12. The composition of claim 9 that undergoes apatite phase decomposition of less than 10% when exposed to conditions of at least 1000° C. for at least 2 hours.]

[13. The composition of claim 12 that undergoes apatite phase decomposition of less than 5% when exposed to conditions of at least 1000° C. for at least 2 hours.]

[14. The composition of claim 12 that undergoes apatite phase decomposition of less than 3% when exposed to conditions of at least 1000° C. for at least 2 hours.]

[15. The composition of claim 12 that undergoes apatite phase decomposition of less than 10% when exposed to conditions of at least 1100° C. for at least 2 hours.]

[16. The composition of claim 12 that undergoes apatite phase decomposition of less than 5% when exposed to conditions of at least 1100° C. for at least 2 hours.]

[17. The composition of claim 12 that undergoes apatite phase decomposition of less than 3% when exposed to conditions of at least 1100° C. for at least 2 hours.]

[18. The composition of claim 12 that undergoes apatite phase decomposition of less than 10% when exposed to conditions of at least 1200° C. for at least 2 hours.]

[19. The composition of claim 12 that undergoes apatite phase decomposition of less than 5% when exposed to conditions of at least 1200° C. for at least 2 hours.]

[20. The composition of claim 12 that undergoes apatite phase decomposition of less than 3% when exposed to conditions of at least 1200° C. for at least 2 hours.]

[21. The composition of claim 12 that undergoes apatite phase decomposition of less than 10% when exposed to conditions of at least 1300° C. for at least 2 hours.]

[22. The composition of claim 12 that undergoes apatite phase decomposition of less than 5% when exposed to conditions of at least 1300° C. for at least 2 hours.]

[23. The composition of claim 12 that undergoes apatite phase decomposition of less than 3% when exposed to conditions of at least 1300° C. for at least 2 hours.]

[24. An article having a dimension of at least 0.5 cm made up of the composition of claim 1.]

[25. The article of claim 24 wherein the particulate apatite is consolidated.]

[26. The article of claim 24, formed into the shape of a prosthesis.]

[27. The article of claim 24 that is a prosthesis.]

[28. The article of claim 24 comprising an exterior coating on a prosthesis.]

[29. The article of claim 28 comprising an exterior coating, on a prosthesis, of at least 0.5 micron in thickness.]

[30. The article of claim 24 having a theoretical density of at least 90%.]

[31. The article of claim 24 having a theoretical density of at least 95%.]

[32. The article of claim 24 having a theoretical density of at least 98%.]

[33. An article having a dimension of at least 0.5 cm made up of the composition of claim 9.]

[34. The article of claim 33 having a porosity of at least 20%.]

[35. The article of claim 33 having a porosity of at least 30%.]

[36. The article of claim 33 having a porosity of at least 50%.]

[37. The article of claim 33 having a porosity of at least 75%.]

[38. The densified article of claim 33 having compressive strength of at least about 150 MPa.]

[39. The densified article of claim 38, having a density of at least about 98%.]

[40. The densified article of claim 33 having compressive strength of at least about 500 MPa.]

[41. The densified article of claim 33 having compressive strength of at least about 700 MPa.]

[42. The densified article of claim 38, having a density of at least about 90%.]

[43. The densified article of claim 38, having a density of at least about 95%.]

[44. The article of claim 24 that is a part of a prosthesis.]

*45. A composition comprising particulate apatite, said particulate apatite having an average apatite crystal size of less than 100 nm, a crystal aspect ratio ranging from spherical to about 2.9:1, and a surface area of at least about 40 $m^2/g$.*

*46. A composition comprising particulate apatite, said particulate apatite having a crystal aspect ratio ranging from spherical to about 2.9:1 and an average particle size small enough that the composition can be sintered to a density of at least 98% at a temperature of less than about 1100° C.*

*47. The composition of claim 45, wherein the particulate apatite has a surface area greater than 60 $m^2/g$.*

*48. The composition of claim 45, wherein the particulate apatite has a surface area greater than 100 $m^2/g$.*

*49. The composition of claim 45, wherein the particulate apatite has an average particle size of less than 1 μm.*

*50. The composition of claim 45, wherein the particulate apatite has an average apatite particle size of less than 0.5 microns.*

*51. The composition of claim 45, wherein the particulate apatite is consolidated.*

*52. The composition of claim 45, wherein the composition can be sintered to a density of at least 98% at a temperature of less than about 1100° C.*

*53. The composition of claim 46, wherein the particulate apatite has an average particle size of less than 1 μm.*

*54. The composition of claim 46, wherein the particulate apatite has an average apatite particle size of less than 0.5 microns.*

*55. The composition of claim 46, wherein the average apatite crystal size is less than 250 nm.*

*56. The composition of claim 46, wherein the average apatite crystal size is less than 100 nm.*

*57. The composition of claim 46, wherein the particulate apatite has a surface area greater than 40 $m^2/g$.*

*58. The composition of claim 46, wherein the particulate apatite has a surface area greater than 60 $m^2/g$.*

*59. The composition of claim 46, wherein the particulate apatite has a surface area greater than 100 $m^2/g$.*

* * * * *